(12) United States Patent
Hendifar

(10) Patent No.: US 11,795,217 B2
(45) Date of Patent: Oct. 24, 2023

(54) INTERLEUKIN-1 INHIBITION FOR COMBINATION TREATMENT OF PANCREATIC CANCER CACHEXIA

(71) Applicant: Cedars-Sinai Medical Center, Los Angeles, CA (US)

(72) Inventor: Andrew Hendifar, Santa Monica, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 298 days.

(21) Appl. No.: 17/207,272

(22) Filed: Mar. 19, 2021

(65) Prior Publication Data

US 2021/0230268 A1 Jul. 29, 2021

Related U.S. Application Data

(62) Division of application No. 16/457,519, filed on Jun. 28, 2019, now Pat. No. 10,975,146.

(60) Provisional application No. 62/691,976, filed on Jun. 29, 2018.

(51) Int. Cl.
| | |
|---|---|
| *C07K 16/24* | (2006.01) |
| *A61K 31/4745* | (2006.01) |
| *A61P 35/00* | (2006.01) |
| *A61K 31/519* | (2006.01) |
| *A61K 31/513* | (2006.01) |

(52) U.S. Cl.
CPC ........ *C07K 16/245* (2013.01); *A61K 31/4745* (2013.01); *A61K 31/513* (2013.01); *A61K 31/519* (2013.01); *A61P 35/00* (2018.01)

(58) Field of Classification Search
CPC .................................................. A61K 39/3955
See application file for complete search history.

(56) References Cited

U.S. PATENT DOCUMENTS

| | | |
|---|---|---|
| 8,034,337 B2 | 10/2011 | Simard |
| 8,187,817 B2 | 5/2012 | Simard et al. |
| 8,242,074 B2 | 8/2012 | Simard |
| 8,388,956 B2 | 3/2013 | Simard |
| 8,388,969 B2 | 3/2013 | Simard |
| 8,546,331 B2 | 10/2013 | Simard |
| 8,679,489 B2 | 3/2014 | Simard |
| 8,784,817 B2 | 7/2014 | Simard |
| 8,865,175 B2 | 10/2014 | Simard et al. |
| 8,956,831 B2 | 2/2015 | Simard |
| 8,962,814 B2 | 2/2015 | Simard |
| 9,181,338 B2 | 11/2015 | Simard |
| 9,809,649 B2 | 11/2017 | Simard |
| 9,840,558 B2 | 12/2017 | Simard |
| 10,202,449 B2 | 2/2019 | Simard |
| 10,294,296 B2 | 5/2019 | Simard |
| 10,899,833 B2 | 1/2021 | Simard |
| 10,975,146 B2 | 4/2021 | Hendifar |
| 11,225,517 B2 | 1/2022 | Giamarellos-Bourboulis et al. |
| 11,390,672 B2 | 6/2022 | Simard |
| 2009/0191149 A1 | 7/2009 | Simard |
| 2009/0214482 A1 | 8/2009 | Beschorner et al. |
| 2010/0040574 A1 | 2/2010 | Simard |
| 2011/0008282 A1 | 1/2011 | Simard |
| 2011/0311547 A1 | 12/2011 | Simard |
| 2012/0021512 A1 | 1/2012 | Simard |
| 2012/0164665 A1 | 1/2012 | Simard |
| 2012/0114598 A1 | 5/2012 | Simard |
| 2013/0195877 A1 | 8/2013 | Simard |
| 2016/0159899 A1 | 6/2016 | Simard |
| 2017/0002071 A1 | 1/2017 | Simard |
| 2019/0127460 A1 | 5/2019 | Simard |
| 2019/0169287 A1 | 6/2019 | Simard |
| 2019/0389946 A1 | 12/2019 | Giamarellos-Bourboulis et al. |
| 2020/0002412 A1 | 1/2020 | Hendifar |
| 2021/0171623 A1 | 6/2021 | Simard |
| 2021/0179704 A1 | 6/2021 | Giamarellos-Bourboulis et al. |
| 2021/0238273 A1 | 8/2021 | Simard |
| 2022/0127353 A1 | 4/2022 | Giamarellos-Bourboulis et al. |
| 2022/0363750 A1 | 11/2022 | Simard |

FOREIGN PATENT DOCUMENTS

| | | |
|---|---|---|
| WO | 2007015128 A1 | 2/2007 |
| WO | 2007132338 A2 | 11/2007 |
| WO | 2007135546 A2 | 11/2007 |
| WO | 2009148575 A1 | 12/2009 |
| WO | 2010030979 A2 | 3/2010 |
| WO | 2011038069 A1 | 3/2011 |
| WO | 2011159976 A2 | 12/2011 |
| WO | 2012027324 A2 | 3/2012 |
| WO | 2013009967 A2 | 1/2013 |
| WO | 2013043973 A2 | 3/2013 |
| WO | 2018150265 A1 | 8/2018 |
| WO | 2019006159 A1 | 1/2019 |
| WO | 2019209923 A1 | 10/2019 |
| WO | 2022073102 A1 | 4/2022 |
| WO | 2022073103 A1 | 4/2022 |
| WO | 2022073104 A1 | 4/2022 |
| WO | 2022073105 A1 | 4/2022 |

OTHER PUBLICATIONS

Bassett et al., Pedometer-Measured Physical Activity and Health Behaviors in U.S. Adults, 2010, Med. Sci. Sports. Exerc., vol. 42(10), pp. 1819-1825.

Cani et al., Changes in Gut Microbiota Control Metabolic Endotoxemia-Induced Inflammation in High-Fat Diet-Induced Obesity and Diabetes in Mice, 2008, Diabetes, vol. 57, pp. 1470-1481.

(Continued)

*Primary Examiner* — Prema M Mertz
(74) *Attorney, Agent, or Firm* — Nixon Peabody LLP; Linda B. Huber; Suwei Zhu

(57) ABSTRACT

A composition for IL-1 inhibition in combination with cancer therapies (e.g., chemotherapeutics including chemotherapy protective drugs) is provided for use in treating pancreatic cancer cachexia in patients, so as to reduce weight loss and improve the quality of life and survival of the patients. In one embodiment, the IL-1 inhibitor is an antibody, such as bermekimab, anakinra, canakinumab, gevokizumab, or rilonacept, administered simultaneously or sequentially with iritenocan, 5-fluorouracil and folinic acid to a pancreatic cancer patient.

17 Claims, 5 Drawing Sheets

(56) References Cited

OTHER PUBLICATIONS

Ellingsgaard et al., Interleukin-6 Enhances Insulin Secretion by Increasing Glucagon-Like Peptide-1 Secretion from L Cells and Alpha Cells, 2011, Nat. Med., vol. 17(11), pp. 1481-1489.
Felix et al., Identification of Serum Proteins Involved in Pancreatic Cancer Cachexia, 2011, Life Sci, vol. 88(5-6), pp. 218-225.
Fried et al., Frailty in Older Adults: Evidence for a Phenotype, 2001, J. Gerontol., A Biol Sci Med Sci, vol. 56A(3), pp. M146-M156.
Furet et al., Differential Adaptation of Human Gut Microbiota to Bariatric Surgery-Induced Weight Loss: Links with Metabolic and Low-Grade Inflammation Markers, 2010, Diabetes, vol. 59, pp. 3049-3057.
Hendifar et al., Evaluating Outcomes of Pancreatic Cancer Patients with Cacehxia, 2014, Journal of Clinical Oncology, vol. 32(15), e15208, Abstract only, Published online Jan. 31, 2017.
Hong et al., MABp1, a First-in-Class True Human Antibody Targeting Interleukin-1alpha in Refractory Cancers: an Open-Label, Phase 1 Dose-Escalation and Expansion Study, 2014, Lancet Oncol., vol. 15(6), pp. 656-666.
Lee et al., Oncogenic KRas Suppresses Inflammation-Associated Senescence of Pancreatic Ductal Cells, 2010, Cancer Cell, vol. 18(5), pp. 448-458.
Ling et al., KrasG12D-Induced IKK2/beta/NF-kappaB Activation by IL-1alpha and p62 Feedforward Loops is Required for Development of Pancreatic Ductal Adenocarcinoma, 2012, Cancer Cell. vol. 21(1): pp. 105-120.
Martignoni et al., Liver Macrophages Contribute to Pancreatic Cancer-Related Cachexia, 2009, Oncol. Reports, vol. 21(2), pp. 363-369.
Martignoni et al., Role of Mononuclear Cells and Inflammatory Cytokines in Pancreatic Cancer-Related Cachexia, 2005, Clin. Cancer Res., vol. 11(16), pp. 5802-5808.
Moses et al., Pro-Inflammatory Cytokine Release by Peripheral Blood Mononuclear Cells from Patients with Advanced Pancreatic Cancer: Relationship to Acute Phase Response and Survival, 2009, Oncol. Report, vol. 21(4), pp. 1091-1095.
Pal et al., Evaluating the Older Patient with Cancer: Understanding Frailty and the Geriatric Assessment, 2010, CA Cancer J. Clin., vol. 60(2), pp. 120-132.
Wang-Gillam et al., Nanoliposomal Irinotecan with Fluorouracil and Folinic Acid in Metastatic Pancreatic Cancer after Previous Gemcitabine-Based Therapy (NAPOLI-1): a Global, Randomised, Open-Label, Phase 3 Trial, 2016, The Lancet, vol. 387(10018), pp. 545-557.
Wigmore et al., Effect of Oral Eicosapentaenoic Acid on Weight Loss in Patients with Pancreatic Cancer, 2000, Nutr. and Cancer, vol. 36(2), pp. 177-184.
Wu et al., Disrupting Cytokine Signaling in Pancreatic Cancer: a Phase I/II Study of Etanercept in Combination with Gemcitabine in Patients with Advanced Disease, 2013, Pancreas, vol. 42(5), pp. 813-818.
CI+A2:A19inicalTrial.gov NCT03207724, Study of Onivyde and 5-FU in Combination with Xilonix for Pancreatic Cancer with Cachexia (OnFX), first posted Jul. 5, 2017, 8 pages.
Hickish et al., MABp1 as a Novel Antibody Treatement for Advanced Colorectal Cancer: A Randomised, Double-Blind, Placebo-Controlled, Phase 3 Study, Lancet Oncology, 2017, vol. 18, pp. 192-201.
Beers & Berkow, The Merck Manual of Diagnosis and Therapy, 17th Edition, 1999, pp. 986-995.

INTERLEUKIN-1 INHIBITION FOR COMBINATION TREATMENT OF PANCREATIC CANCER CACHEXIA

CROSS-REFERENCE TO RELATED APPLICATIONS

This application claims the benefit of priority under 35 U.S.C. § 121 as a divisional of U.S. patent application Ser. No. 16/457,519, filed Jun. 28, 2019, which includes a claim of priority under 35 U.S.C. § 119(e) to U.S. provisional patent application No. 62/691,976, filed Jun. 29, 2018, the entirety of which is hereby incorporated by reference.

STATEMENT REGARDING FEDERALLY SPONSORED RESEARCH OR DEVELOPMENT

This invention was made with Government support under grant no. TR000124 awarded by the National Institutes of Health. The Government has certain rights in the invention.

FIELD OF INVENTION

This invention relates to therapies for improving weight maintenance and quality of life in pancreatic cancer patients.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Despite decades of clinical trials, the prognosis for advanced pancreatic cancer is poor. The 5-year survival has remained close to 5% and unchanged despite improvements in chemotherapeutics, surgical outcomes, and diagnostic techniques. Advanced pancreatic adenocarcinoma is characterized by progressive weight loss and nutritional deterioration. It is estimated that up to 80% of these patients are present with cachexia (e.g., weakness and wasting of the body involving marked weight loss and muscle loss). This syndrome has been linked not only to survival, but also to alterations in host defenses, functional ability, and quality of life.

Despite its clinical ubiquity, the mechanisms and therapeutic importance of pancreatic cancer cachexia are not understood. Pancreatic cancer patients have the highest rate of muscle wasting and weight loss of all advanced cancers. This syndrome likely contributes to chemotherapy resistance and poor outcomes.

New insights into this clinical dilemma have been gained over the past decade. Dysregulation in the neuropeptide pathway of leptin and neurotensin, which are involved in body weight regulation, have been described. Lipid mobilizing factors (LMF) and protein-mobilizing factors also play a role by inducing lipolysis and proteolysis. Lipid and fat degradation is stimulated through release of proinflammatory cytokines and tumor-derived factors. These factors include tumor necrosis factor-alpha (TNF-α), interleukin-6, glucagon-like peptide-1 (GLP-1), and tumor secretory factor ZAG.

Other than multi-agent cytotoxic therapy, there have been no treatment advances for pancreatic cancer or its associated cachexia. Despite the availability of effective chemotherapy, only between 15-40% of pancreatic cancer patients are able to receive second line treatment. Importantly, cachexia and its associated fatigue and deconditioning, may explain the difficulty in providing continued therapy after progression in the first-line. Recently, an early phase study of a JAK inhibitor demonstrated survival benefit in a cohort of pancreatic cancer patients with elevated C-reactive protein (CRP). This appears to highlight the importance of oncoinflammation in pancreatic cancer and anti-inflammatory therapies.

Therefore, it is an objective of the present invention to provide a composition for cancer therapies and/or to improve the quality of life and survival of these patients.

It is another objective of the present invention to provide a method of ameliorating cachexia and improving the health of cancer patients (e.g., pancreatic cancer patients).

SUMMARY OF THE INVENTION

The following embodiments and aspects thereof are described and illustrated in conjunction with compositions and methods which are meant to be exemplary and illustrative, not limiting in scope.

Compositions capable of interleukin-1 inhibition are provided for use in combination with cancer therapeutics in the treatment of cancer cachexia, e.g., in subjects with advanced pancreatic cancer who exhibits greater than 5% unexplained weight loss within the recent six months.

Various embodiments provide a composition, a combination or a system for treating, inhibiting, and/or reducing the severity or likelihood of pancreatic cancer, cancer cachexia, or both in a subject, which contains an inhibitor of the interleukin 1 (IL-1) pathway (e.g., an inhibitor of IL-1α, an inhibitor of IL-1β, and/or an inhibitor of IL-1 receptor) in combination with one, two or more of chemotherapeutic agents and/or a chemotherapy protective drug, wherein they may be in one composition with a pharmaceutically acceptable excipient (e.g., in liquid form or lyophilized), or any one, two, three or all four of them may be separately provided in a kit. Further embodiments provide a composition, a combination or a system containing an anti-IL-1α antibody, an anti-IL-1β antibody or an IL-1 receptor antagonist in combination with irinotecan (e.g., in the form of nanoliposome, such as ONIVYDE), 5-fluorouracil and folinic acid. Some embodiments provide an antibody against IL-1α, an antibody against IL-1α receptor, or both, are combined with ONIVYDE (nanoliposomal irinotecan), 5-fluorouracil and folinic acid in an effective amount to treat subjects with cancer (e.g., pancreatic cancer) and/or treat cancer-related cachexia (e.g., pancreatic cancer cachexia). An exemplary embodiment includes an effective amount of XILONIX, a monoclonal antibody against IL-1α, is administered concurrently or sequentially with ONIVYDE, 5-fluorouracil and folinic acid to a subject with pancreatic cancer, so as to reduce the likelihood, ameliorate or treat cancer cachexia, or cancer cachexia and cancer, in the subject. Another embodiment provides an effective amount of anakinra, canakinumab or rilonacept is administered with ONIVYDE, 5-fluorouracil and folinic acid to a subject with pancreatic cancer, so as to reduce the likelihood, ameliorate or treat cancer cachexia, or cancer cachexia and cancer, in the subject.

Various embodiments provide methods of treating, inhibiting, and/or reducing the severity or likelihood of cancer, cancer cachexia, or both in a subject by administering an effective amount of an inhibitor of IL-1 pathway, which includes an inhibitor of IL-1α, an inhibitor of IL-1β, and/or an inhibitor of IL-1 receptor (IL-1R). In some aspects, the cancer and/or cancer cachexia is pancreatic cancer and/or pancreatic cancer cachexia. A method for treating, inhibiting, reducing the severity or likelihood of cancer cachexia is provided, including administering to a cancer subject with cachexia an effective amount of an inhibitor of IL-1/IL-1R and an effective amount of chemotherapeutics including chemotherapy protective drugs. An embodiment provides that the method of treating, inhibiting, and/or reducing the severity or likelihood of pancreatic cancer, cancer cachexia, or both in a subject includes, or consists of, administering to the subject an effective amount of an antibody that binds IL-1α, IL-1β or IL-1 receptor in combination with ONIVYDE (nanoliposomal irinotecan), 5-fluorouracil and folinic acid. In various embodiments, the subject has advanced or locally advanced pancreatic cancer.

Other embodiments provide methods for treating, inhibiting, reducing the severity or likelihood of cancer cachexia is provided, which include administering to a cancer subject with cachexia an effective amount of an inhibitor of IL-1/IL-1 receptor, wherein the subject has been treated with chemotherapeutics such as irinotecan, 5-fluorouracil and folinic acid for advanced pancreatic cancers. Further aspects of these embodiments include selecting a subject who has cachexia or pancreatic cancer, and/or selecting a subject who has cachexia or pancreatic cancer and whose response to chemotherapeutics such as irinotecan, 5-fluorouracil and folinic acid has been ineffective.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

FIG. 4A depicts those of subject ID (SID) 1, 3, 5, 6 and 7; FIG. 4B depicts those of SID 8, 9, 10, 12 and 13; and FIG. 4C depicts those of SID 14, 15, 16, 17 and 18.

FIG. 5A depicts those of subject ID (SID) 1, 3, 5, 6 and 7; FIG. 5B depicts those of SID 8, 9, 10, 12 and 13; and FIG. 5C depicts those of SID 14, 15, 16, 17 and 18.

DESCRIPTION OF THE INVENTION

Figure 1:
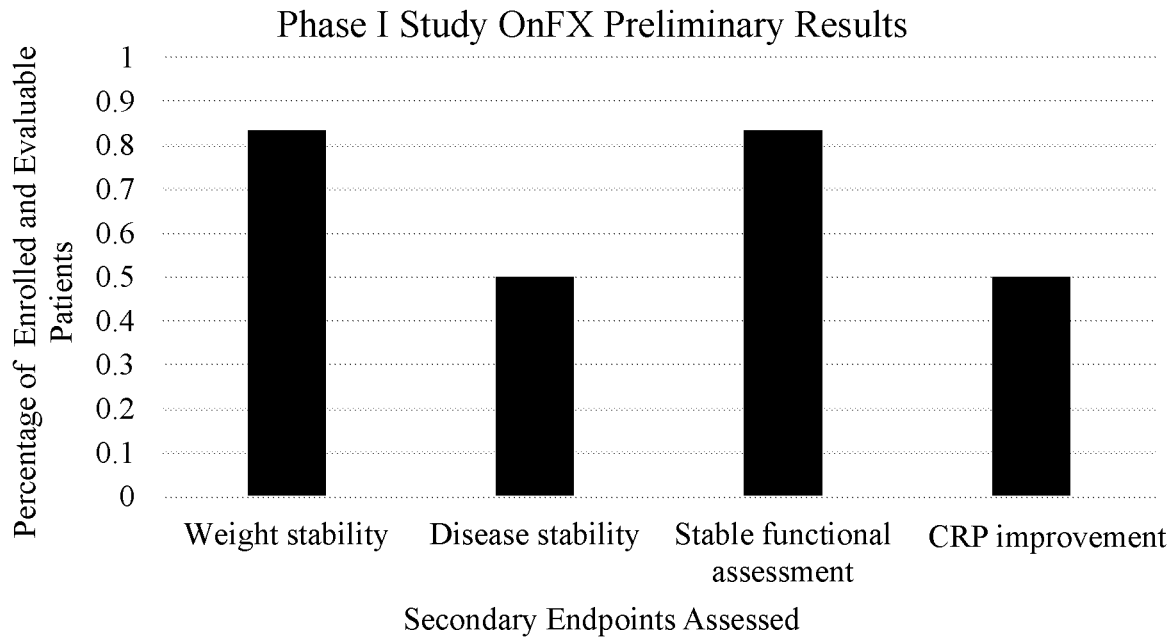
FIG. 1 is a bar graph showing the percentage (fraction) of patients, out of the six evaluable enrolled patient, having weight stability, disease stability, stable functional assessment, or C-reactive protein (CRP) elevation, at the secondary endpoints in the phase one study described in Example 1.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., Revised, J. Wiley & Sons (New York, N.Y. 2006); March, *Advanced Organic Chemistry Reactions, Mechanisms and Structure* 7$^{th}$ ed., J. Wiley & Sons (New York, N.Y. 2013); and Sambrook and Russel, *Molecular Cloning: A Laboratory Manual* 4$^{th}$ ed., Cold Spring Harbor Laboratory Press (Cold Spring Harbor, N.Y. 2012), provide one skilled in the art with a general guide to many of the terms used in the present application. For references on how to prepare antibodies, see D. Lane, *Antibodies: A Laboratory Manual* 2nd ed. (Cold Spring Harbor Press, Cold Spring Harbor N.Y., 2013); Kohler and Milstein, (1976) Eur. J. Immunol. 6: 511; Queen et al. U.S. Pat. No. 5,585,089; and Riechmann et al., Nature 332: 323 (1988); U.S. Pat. No. 4,946,778; Bird, Science 242:423-42 (1988); Huston et al., Proc. Natl. Acad. Sci. USA 85:5879-5883 (1988); Ward et al., Nature 334:544-54 (1989); Tomlinson I. and Holliger P. (2000) Methods Enzymol, 326, 461-479; Holliger P. (2005) Nat. Biotechnol. September; 23(9):1126-36).

One skilled in the art will recognize many methods and materials similar or equivalent to those described herein, which could be used in the practice of the present invention. Indeed, the present invention is in no way limited to the methods and materials described. For purposes of the present invention, the following terms are defined below.

A "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets.

The terms "treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder, such as weight loss or muscle loss resulting from cancer cachexia. Treatment is generally "effective" if one or more symptoms or clinical markers are reduced. Alternatively, treatment is "effective" if the progression of a disease or condition is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

"Beneficial results" or "desired results" may include, but are in no way limited to, lessening or alleviating the severity of the disease condition, preventing the disease condition from worsening, curing the disease condition, preventing the disease condition from developing, lowering the chances of a patient developing the disease condition, decreasing morbidity and mortality, and prolonging a patient's life or life expectancy. As non-limiting examples, "beneficial results" or "desired results" may be alleviation of one or more symptom(s), diminishment of extent of the deficit, stabilized (i.e., not worsening) state of cancer progression, delay or slowing of metastasis or invasiveness, and amelioration or palliation of symptoms associated with the cancer.

The term "administering," refers to the placement an agent as disclosed herein into a subject by a method or route which results in at least partial localization of the agents at a desired site.

The term "antibody" refers to an intact immunoglobulin or to a monoclonal or polyclonal antigen-binding fragment with the Fc (crystallizable fragment) region or FcRn binding fragment of the Fc region, referred to herein as the "Fc fragment" or "Fc domain". Antigen-binding fragments may be produced by recombinant DNA techniques or by enzymatic or chemical cleavage of intact antibodies. Antigen-binding fragments include, inter alia, Fab, Fab', F(ab')2, Fv, dAb, and complementarity determining region (CDR) fragments, single-chain antibodies (scFv), single domain antibodies, chimeric antibodies, diabodies and polypeptides that contain at least a portion of an immunoglobulin that is sufficient to confer specific antigen binding to the polypeptide. The Fc domain includes portions of two heavy chains contributing to two or three classes of the antibody. The Fc domain may be produced by recombinant DNA techniques or by enzymatic (e.g. papain cleavage) or via chemical cleavage of intact antibodies.

The term "antibody fragment," refers to a protein fragment that comprises only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment which consists of a VH domain; (vii) isolated CDR regions; (viii) F(ab')2 fragments, a bivalent fragment including two Fab' fragments linked by a disulphide bridge at the hinge region; (ix) single chain antibody molecules (e.g., single chain Fv; scFv); (x) "diabodie" with two antigen binding sites, comprising a heavy chain variable domain (VH) connected to a light chain variable domain (VL) in the same polypeptide chain; (xi) "linear antibodies" comprising a pair of tandem Fd segments (VH—CH1-VH—CH1) which, together with complementary light chain polypeptides, form a pair of antigen binding regions.

"Selectively binds" or "specifically binds" refers to the ability of an antibody or antibody fragment thereof described herein to bind to a target, such as a molecule present on the cell-surface, with a $K_D$ $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. Specific binding can be influenced by, for example, the affinity and avidity of the polypeptide agent and the concentration of polypeptide agent. The person of ordinary skill in the art can determine appropriate conditions under which the polypeptide agents described herein selectively bind the targets using any suitable methods, such as titration of a polypeptide agent in a suitable cell binding assay.

"Ineffective" treatment refers to when a subject is administered a treatment and there is less than 1%, 5%, or 10% improvement in symptoms.

A "cancer" or "tumor" as used herein refers to an uncontrolled growth of cells which interferes with the normal functioning of the bodily organs and systems, and/or all neoplastic cell growth and proliferation, whether malignant or benign, and all pre-cancerous and cancerous cells and tissues. Included in this definition are benign and malignant cancers, as well as dormant tumors or micrometastatses. As used herein, the term "carcinoma" refers to a cancer arising from epithelial cells. As used herein, the term "invasive" refers to the ability to infiltrate and destroy surrounding tissue. Melanoma is an invasive form of skin tumor. Examples of cancer include, but are not limited to, pancreatic cancer, B-cell lymphomas (Hodgkin's lymphomas and/or non-Hodgkins lymphomas), brain tumor, breast cancer, colon cancer, lung cancer, hepatocellular cancer, gastric cancer, cervical cancer, ovarian cancer, liver cancer, bladder cancer, cancer of the urinary tract, thyroid cancer, renal cancer, carcinoma, melanoma, head and neck cancer, brain cancer, and prostate cancer, including but not limited to androgen-dependent prostate cancer and androgen-independent prostate cancer. In some embodiments, the cancer is pancreatic cancer. In various embodiments, a subject in the disclosed methods herein is diagnosed or shows symptoms of pancreatic cancer.

"Cachexia" generally refers to 5% or greater than unexplained weight loss within 6 months, which is typically prior to screening visit of a patient; for example, a cancer patient. Other symptoms of cachexia include muscle loss.

"XILONIX," refers to the trademark of a monoclonal (IgG1k) antibody, bermekimab, which targets interleukin-1α. Bermekimab (XILONIX) has been shown to be safe and effective in several clinical studies of patients who have not responded to standard chemotherapy. In a recent phase 1 study, bermekimab, in patients with refractory cancers had significant symptomatic improvement with decreased constitutional symptoms, and extended survival. There was no dose limiting toxicity and associated grade ¾ toxicities include: proteinuria (21%), nausea (13%), and fatigue (13%). 61 patients (62% of evaluable patients) were considered to have a positive DXA outcome as defined for the responder endpoint, with an average LBM change of 2.1±2.8 kg (median 1.2 [IQR 0.5 to 2.0] kg). The average gain of 2 kg of lean body mass is extraordinary and suggests an application to our patient population. The final dose selected was 3.75 mg/kg every 2 weeks. Many patients with refractory cancers had significant symptomatic improvement with decreased constitutional symptoms. A significant number of patients had increased lean body mass (p=0.02), decreased constitutional symptoms (fatigue p=0.008, pain p=0.025, and appetite loss p=0.020), and improved survival. More recently, a phase III clinical trial conducted in Europe, comparing XILONIX to best supportive care in 309 patients with metastatic colorectal cancer demonstrated improved survival and other outcomes. Included in the study were patients who did not respond to oxaliplatin and irinotecan and had symptoms including functional impairment, weight loss, and elevated systematic inflammation, were included in the study. The study was randomized 2:1 where the primary outcome was response to treatment and secondary outcomes included symptom control, quality-of-life and systemic inflammation. Safety and tolerability was also assessed. Patients in the treatment group demonstrated a 33% response compared to a 19% response for placebo (p=0.0045). It also was significant for improved control of paraneoplastic thrombocytosis and reduced systemic inflammation. Safety and tolerability resulted in a 26% relative reduction in the number of SAEs (p=0.062).

Various embodiments provide a composition, a combination or a system, which contains an inhibitor of IL-1 pathway (e.g., an inhibitor of IL-1α, an inhibitor of IL-1β, and/or an inhibitor of IL-1 receptor) in combination with one, two or more chemotherapeutic agents (including antineoplastic drugs) and/or a chemotherapy protective drug. These may be in one composition with a pharmaceutically acceptable excipient (e.g., in liquid form or lyophilized), or any one, two, three or all four of them may be separately provided in a kit. In some embodiments, a composition, a combination, or a system is provided including bermekimab in combination with any one, any two or all three of irinotecan, 5-fluorouracil, and folinic acid. In further embodiments, a composition, a combination, or a system is provided including, or consisting of, bermekimab, irinotecan, 5-fluorouracil, and folinic acid, in an amount effective to reduce tumor target lesion size, reduce C-reactive protein level, reduce cancer antigen 19-9 level, or a combination thereof.

Compositions capable of inhibiting interleukin-1 (including IL-1α, IL-1β and IL-1 receptor) pathway are provided for use in combination with cancer therapeutics in the treatment of cachexia in patients with cancer, especially advanced pancreatic cancer. IL-1α is associated with the promotion of angiogenesis in the tumor as well as provision of blood supply resulting in tumor growth. IL-1α affects the body's metabolism, thus resulting in fatigue, anxiety and anorexia. Both acute and chronic inflammation is associated with cancer and especially pancreatic cancer. Onco-inflammation is hypothesized to lead to cancer cachexia as well as stromal proliferation that cause chemotherapy resistance. IL-1α is an important mediator of this phenomenon.

Inhibitors of IL-1 Pathway

Inhibitors of IL-1 pathway can be a small molecule, a nucleic acid, a peptide or a protein capable of binding IL-1α, IL-1β, or IL-1 receptor, and/or inhibiting the production of IL-1α, IL-1β, or IL-1 receptor.

Exemplary inhibitors of IL-1α include bermekimab (XILONIX), which is a monoclonal antibody targeting IL-1α, thereby neutralizing the effect of IL-1α. XILONIX has been shown to be safe and effective in several clinical studies of patients who have not responded to standard chemotherapy.

Exemplary inhibitors of IL-1β include a neutralizing monoclonal anti-IL-1β antibody canakinumab. Canakinumab is a human monoclonal antibody targeted at interleukin-1 beta, which has a longer half-life than anakinra. Other exemplary inhibitors of IL-1 pathway include caspase 1 inhibitors such as histone deacetylase inhibitor givinostat (ITF2357), which inhibits the production of IL-1β.

Additional embodiments provide an inhibitor of IL-1 pathway is IL-1 receptor antagonist, which can be similar to IL-1α or IL-1β but having no IL-1-like activity and antagonizing IL-1 by binding to its cell surface receptor. An exemplary IL-1 receptor antagonist is anakinra. Anakinra, composed of 153 amino acid residues, is a recombinant non-glycosylated form of the human interleukin-1 receptor antagonist, which has an extra methionine residue at the amino terminus, compared to the native IL-1 receptor antagonist; and it can be manufactured by using the *E. coli* expression system. Anakinra is available commercially for use in patients with rheumatoid arthritis and other forms of inflammatory arthritis. However, its relatively modest effect on inflammatory arthritis in rheumatoid arthritis compared with other biologic agents, such as the TNF inhibitors, has resulted in their being used only rarely for this disease. Unlike conventional disease-modifying antirheumatic drugs (DMARDs; e.g., methotrexate), anakinra is not recommended in a combination regimen with a TNF inhibitor or other biologic agents because of an increased frequency of serious adverse events, including serious infections.

Yet other embodiments provide an inhibitor of IL-1 pathway is decoy receptor, and an exemplary soluble decoy receptor is rilonacept. Rilonacept is a dimeric fusion protein consisting of the ligand-binding domains of the extracellular portions of the human interleukin-1 receptor component and IL-1 receptor accessory protein (IL-1RAcP) linked in-line to the Fc portion of human IgG1; and it can be expressed in recombinant Chinese hamster ovary (CHO) cells. The bispecific arms of rilonacept bind IL-1β.

Yet another embodiment provides exemplary agents for reducing IL-1 activity include gevokizumab (a neutralizing anti-IL-1β IgG2 mAb, also known as VPM087), LY2189102 (a neutralizing anti-IL-1β IgG1 mAb), MABp1 (a neutralizing anti-IL-1α IgG1 mAb), MEDI-8968 (a blocking antibody to IL-1RI), CYT013 (a therapeutic vaccine targeting IL-1β), EBI-005 (a chimeric IL-1Ra-IL-1β), CMPX-1023 (an alphabody), and VX-765 (an oral caspase 1 inhibitor).

Chemotherapeutic Agents and Chemoprotective Agents

Various embodiments provide a composition, a combination or a system containing an inhibitor of IL-1 pathway with one, two or more chemotherapeutic agents, and one or more chemotherapy protective drugs.

An exemplary composition, combination or system is provided including (1) an antibody, antibody fragment or protein selected from the group consisting of bermekimab (XILONIX), canakinumab, anakinra, rilonacept, and gevokizumab; (2) nanoliposomal irinotecan (ONIVYDE); (3) 5-fluorouracil and (4) folinic acid. A recent advance in the treatment of second-line pancreatic cancer includes the FDA approval of nanoliposomal irinotecan (nal-IRI "ONIVYDE") in addition to 5-fluorouracil (5FU) and folinic acid (FA). In the pivotal phase 3 trial, patients were randomized to single agent 5-fluorouracil vs the combination of 5-fluorouracil and ONIVYDE. After 313 events, median overall survival in patients assigned nanoliposomal irinotecan plus 5FU/FA was 6.1 months (95% CI 4.8-8.9) vs 4.2 months (3.3-5.3) with 5FU/FA (hazard ratio 0.67, 95% CI 0.49-0.92; p=0.012). This combination was particularly effective in patients able to tolerate 80% of the recommended dose and receive at least 6 weeks of chemotherapy. The grade 3 or 4 adverse events that occurred most frequently in the 117 patients assigned nanoliposomal irinotecan plus 5FU and folinic acid were neutropenia (32 [27%]), diarrhoea (15 [13%]), vomiting (13 [11%]), and fatigue (16 [14%]).

Exemplary chemotherapeutics (or chemotherapeutic agents) include one or more of irinotecan, nanoliposomal irinotecan (Nal-IRI), 5-fluorouracil, Temozolomide, Actinomycin, Alitretinoin, All-trans retinoic acid, Azacitidine, Azathioprine, Bevacizumab, Bexatotene, Bleomycin, Bortezomib, Carboplatin, Capecitabine, Cetuximab, Cisplatin, Chlorambucil, Cyclophosphamide, Cytarabine, Daunorubicin, Docetaxel, Doxifluridine, Doxorubicin, liposome-encapsulated Doxorubicin such as Doxil (pegylated form), Myocet (nonpegylated form) and Caelyx, Epirubicin, Epothilone, Erlotinib, Etoposide, Fluorouracil, Gefitinib, Gemcitabine, Hydroxyurea, Idarubicin, Imatinib, Ipilimumab, Mechlorethamine, Melphalan, Mercaptopurine, Methotrexate, Mitoxantrone, Ocrelizumab, Ofatumumab, Oxaliplatin, Paclitaxel, Taxol, Abraxane, Genexol, Protein-Bound Paclitaxel, Nab-Paclitaxel, Panitumab, Pemetrexed, Rituximab, Tafluposide, Teniposide, Tioguanine, Topotecan, Tretinoin, Valrubicin, Vemurafenib, Vinblastine, Vincristine, Vindesine, Vinorelbine, Vorinostat, Romidepsin, 6-mercaptopurine (6-MP), Cladribine, Clofarabine, Floxuridine, Fludarabine, Pentostatin, Mitomycin, ixabepilone, Estramustine, prednisone, methylprednisolone, and dexamethasone. In various embodiments, the chemotherapeutic agent is a platinum-based antineoplastic agent. Examples of the platinum-based antineoplastic agent include but are not limited to oxaliplatin, cisplatin, lipoplatin (a liposomal version of cisplatin), carboplatin, satraplatin, picoplatin, nedaplatin, and triplatin, and their functional equivalents, analogs, derivatives, variants or salts.

Exemplary Chemotherapy Protective Drugs Include Folinic Acid, Amifostine, Dexrazoxane, and Mesna.

In some embodiments, a composition, a combination or a system is provided including bermekimab (XILONIX), anakinra, canakinumab and/or rilonacept, in combination with nanoliposomal irinotecan (Nal-IRI), 5-fluorouracil, and folinic acid.

Method of Use

Various embodiments provide methods for treating, inhibiting the progression and/or reducing the severity or likelihood of cancer in a subject and/or cancer cachexia in a subject having been determined, diagnosed or showing symptoms of cancer, which includes administering an effective amount of any inhibitor of the IL-1 pathway described above. Further embodiments provide these methods further includes administering one or more of the chemotherapeutic agents and chemotherapy protective drugs. Additional embodiments provide administering an inhibitor of the IL-1 pathway to a subject with cancer or cancer cachexia, wherein the subject has been administered one or more chemotherapeutics and chemotherapy protective drug (such as irinotecan, 5-fluorouracil and folinic acid), in an effective amount to treat or reduce the severity of cancer or cancer cachexia. Further aspects of these methods provide the subject's response to the one or more chemotherapeutics and chemotherapy protective drug (such as irinotecan, 5-fluorouracil and folinic acid) has been ineffective, prior to the administration of the inhibitor of the IL-1 pathway.

Some embodiments provide the methods are for treating, inhibiting the progression and/or reducing the severity or likelihood of pancreatic cancer in a subject and/or pancreatic cancer cachexia in a subject having been determined, diagnosed or showing symptoms of pancreatic cancer, which includes administering an effective amount of an inhibitor of the IL-1 pathway in combination with one, two or more chemotherapeutic agents, and one or more chemotherapy protective drugs. "In combination with" herein refers to concurrent it sequential administration, or a combination of both in repetitive administrations.

Other embodiments provide methods are for treating, inhibiting the progression and/or reducing the severity or likelihood of pancreatic cancer in a subject and/or pancreatic cancer cachexia in a subject having been determined, diagnosed or showing symptoms of pancreatic cancer, which includes administering an effective amount of an inhibitor of the IL-1 pathway to the subject and the subject has been administered one or more chemotherapeutics and chemotherapy protective drug (such as irinotecan, 5-fluorouracil and folinic acid). Some aspects provide the subject's response to the one or more chemotherapeutics and chemotherapy protective drug (such as irinotecan, 5-fluorouracil and folinic acid) was ineffective, prior to the administration of the inhibitor of the IL-1 pathway.

Also provided are methods of selecting a subject with pancreatic cancer or pancreatic cancer cachexia and treating, reducing the severity or inhibiting the progression of the pancreatic cancer and/or the pancreatic cancer cachexia in the subject by administering to the subject an inhibitor of the IL-1 pathway (e.g., anti-IL-1α antibody, anti-IL-1β antibody, or IL-1 receptor antagonist), and optionally in combination with or further administering chemotherapeutic agents (e.g., irinotecan, 5-fluoroucil) and/or chemotherapy protective agents (e.g., folinic acid). In some aspects, the subject has received chemotherapeutic agents and/or chemotherapy protective agents prior to the administration of the inhibitor of the IL-1 pathway. In further aspects, the subject's response to the chemotherapeutic agents and/or chemotherapy protective agents was ineffective prior to the administration of the inhibitor of the IL-1 pathway.

Provided herein is a method for treating, inhibiting and/or reducing the severity of cancer cachexia in a subject in need thereof, or treating, inhibiting and/or reducing the severity of cancer. The method comprises, consists or consists essentially of administering an effective amount of an inhibitor of the interleukin-1 pathway (including an inhibitor of IL-1α, an inhibitor of IL-1β, and an interleukin-1 receptor antagonist) to a subject with advanced pancreatic cancer. In some embodiments, the method further comprises administering cancer therapeutics in a subject. In one embodiment, the inhibitor of IL-1 and/or the IL-1 receptor antagonist is administered with one or more chemotherapeutics, one or more chemotherapy protective drugs, or a combination thereof. In one embodiment, the IL-1 inhibitor is XILONIX, which is administered at dosages and frequencies described herein. In one embodiment, the subject has advanced pancreatic cancer and suffers from, or has a high likelihood of developing, cancer cachexia. In another embodiment, the subject has received chemotherapeutic agents and/or chemotherapy protective drugs prior to the administration of the inhibitor of the IL-1 pathway, and the subject's response to them was ineffective.

Also provided herein is a method for treating, inhibiting and/or reducing the severity of cancer cachexia in a subject in need thereof. The method comprises, consists or consists essentially of administering an effective amount of an inhibitor of IL-1 or IL-1 receptor, an effective amount of a chemotherapeutics, and an effective amount of a chemotherapy protective drug to the subject, wherein the subject is diagnosed or suffers from cachexia associated with pancreatic cancer.

In one embodiment, a method for treating, inhibiting and/or reducing the severity of cancer cachexia in a subject in need thereof is provided. The method comprises, consists or consists essentially of administering (1) an effective amount of one or more IL-1/IL-1R inhibitors of bermekimab (XILONIX), anakinra, canakinumab and rilonacept, (2) an effective amount of irinotecan (e.g., nanoliposomal irinotecan), (3) an effective amount 5-fluorouracil, and (4) an effective amount of folinic acid, to a subject having pancreatic cancer and exhibiting symptoms, or likely to develop, cachexia. The one or more IL-1/IL-1R inhibitors may be administered concurrently, prior to, or subsequently to irinotecan, 5-fluorouracil and folinic acid.

In another embodiment, a method for treating, inhibiting and/or reducing the severity of cancer cachexia in a subject in need thereof is provided. The method comprises, consists or consists essentially of administering an effective amount of one or more of XILONIX, anakinra, canakinumab and rilonacept, to a subject having pancreatic cancer and exhibiting symptoms, or likely to develop, cachexia, wherein the subject has been administered with chemotherapeutics such as irinotecan and 5-fluorouracil and with chemotherapy protective drugs such as folinic acid.

Further provided herein are methods for treating, inhibiting and/or reducing the severity of cancer cachexia in a subject in need thereof, which includes administering an effective amount of one or more of XILONIX, anakinra, canakinumab and rilonacept, an effective amount of irinotecan, 5-fluorouracil and folinic acid, to a subject with advanced pancreatic cancer who has had greater than 5% unexplained weight loss in the prior six months. In some embodiments, the method further includes selecting a human patient with advanced pancreatic cancer who has had greater than 5% unexplained weight loss within the prior six months. In other embodiments, the method further includes measuring fatigue level, weight stability, functional assessment, the level of C-reactive protein, or a combination thereof.

Patient Population

Various embodiments provide the disclosed composition for IL-1 pathway inhibition is used in combination with chemotherapeutics and/or chemotherapy protective drugs in a subject with cancer cachexia. In some embodiments, the subject is a human patient having an advanced or locally advanced pancreatic cancer who exhibits cachexia (greater than 5% unexplained weight loss within 6 months prior to screening visit). In various embodiments, the subject does not have a history of hypersensitivity to compounds of similar chemical or biologic composition to XILONIX or ONIVYDE. In further embodiments, the methods disclosed herein include selecting a subject with cancer (e.g., pancreatic cancer) and/or exhibiting cancer cachexia, and administering an effective amount of the composition for inhibiting IL-1 pathway.

Non-limiting examples of cancers for treatment of cancer cachexia include pancreatic cancer, melanoma (e.g., metastatic malignant melanoma), renal cancer (e.g. clear cell carcinoma), prostate cancer (e.g. hormone refractory prostate adenocarcinoma), breast cancer, colon cancer, neuroendocrine neoplasms, and lung cancer (e.g. non-small cell lung cancer).

Dosage

In some embodiments, the effective amounts of an inhibitor of the IL-1 pathway in the compositions or in the methods can be in the range of about 10-50 mg/day, 50-100 mg/day, 100-150 mg/day, 150-200 mg/day, 100-200 mg/day, 200-300 mg/day, 300-400 mg/day, 400-500 mg/day, 500-600 mg/day, 600-700 mg/day, 700-800 mg/day, 800-900 mg/day, 900-1000 mg/day, 1000-1100 mg/day, 1100-1200 mg/day, 1200-1300 mg/day, 1300-1400 mg/day, 1400-1500 mg/day, 1500-1600 mg/day, 1600-1700 mg/day, 1700-1800 mg/day, 1800-1900 mg/day, 1900-2000 mg/day, 2000-2100 mg/day, 2100-2200 mg/day, 2200-2300 mg/day, 2300-2400 mg/day, 2400-2500 mg/day, 2500-2600 mg/day, 2600-2700 mg/day, 2700-2800 mg/day, 2800-2900 mg/day or 2900-3000 mg/day. In one embodiment of the invention, the inhibitor of the IL-1 pathway is XILONIX, which binds IL-1α; and/or it is anakinra, canakinumab, rilonacept or gevokizumab (VPM087).

In further embodiments, the effective amount of an inhibitor of the IL-1 pathway for use with the claimed methods may be in the range of 0.01-0.05 mg/kg, 0.05-0.1 mg/kg, 0.1-1 mg/kg, 1-5 mg/kg, 5-10 mg/kg, 10-50 mg/kg, 50-100 mg/kg. In additional embodiments, the effective amount of the inhibitor of the IL-1 pathway is about 1-2 mg/kg, 2-3 mg/kg, 3-4 mg/kg, 4-5 mg/kg, 5-6 mg/kg, 6-7 mg/kg, 7-8 mg/kg, 8-9 mg/kg, 9-10 mg/kg, 10-11 mg/kg, 11-12 mg/kg, 12-13 mg/kg, 13-15 mg, 15-20 mg/kg or 20-25 mg/kg. In additional embodiments, the effective amount of the inhibitor of IL-1/IL-1R is any one or more of about 100-125 mg, 125-150 mg, 150-175 mg, 160-170 mg, 175-200 mg, 155-165 mg, 160-165 mg, 165-170 mg, 155-170 mg, or combinations thereof. In one embodiment, the inhibitor of the IL-1 pathway is XILONIX, which binds IL-1α; or it is gevokizumab (VPM087), anakinra, canakinumab or rilonacept. Various embodiments provide an effective amount of a chemotherapeutic agent and/or a chemotherapy protective drug for use with the claimed methods or in the disclosed composition or combination is each selected in the range of 1-5 mg/kg, 5-10 mg/kg, 10-50 mg/kg, 50-100 mg/kg, 100-150 mg/kg, 150-200 mg/kg, 100-200 mg/kg, 200-300 mg/kg, 300-400 mg/kg, 400-500 mg/kg, 500-600 mg/kg, 600-700 mg/kg, 700-800 mg/kg, 800-900 mg/kg or 900-1000 mg/kg; or 0.1-1 mg/m$^2$, 1-10 mg/m$^2$, 10-20 mg/m$^2$, 20-30 mg/m$^2$, 30-40 mg/m$^2$, 40-50 mg/m$^2$, 50-60 mg/m$^2$, 60-70 mg/m$^2$, 70-80 mg/m$^2$, 80-90 mg/m$^2$, 90-100 mg/m$^2$, 100-200 mg/m$^2$, 200-300 mg/m$^2$, 300-400 mg/m$^2$, 400-500 mg/m$^2$, 500-600 mg/m$^2$, 600-700 mg/m$^2$, 700-800 mg/m$^2$, 800-900 mg/m$^2$, 900-1,000 mg/m$^2$, 1,000-1,200 mg/m$^2$, 1,200-1,400 mg/m$^2$, 1,400-1,600 mg/m$^2$, 1,600-1,800 mg/m$^2$, 1,800-2,000 mg/m$^2$, 2,000-2,500 mg/m$^2$, 2,500-3,000 mg/m$^2$, 3,000-3,500 mg/m$^2$, 3,500-4,000 mg/m$^2$, 4,000-4,500 mg/m$^2$, 4,500-5,000 mg/m$^2$. In one embodiment, the chemotherapeutics include ONIVYDE (nanoliposomal irinotecan) and 5-fluorouracil, and the chemotherapy protective drug includes folinic acid (leucovorin).

In one embodiments, bermekimab (XILONIX) is administered between 5-10 mg/kg (e.g., about 7.5 mg/kg) intravenously once every two weeks to an adult subject; and in further aspect, the subject is monitored for safety and efficacy data, and if safe, continued dosage of similar or lower amounts of bermekimab is administered, and if toxicity appears, reducing amounts and/or frequency of bermekimab is administered or discontinued. Further embodiments provide that bermekimab is administered at 3.75 mg/kg or more intravenously every other week. In some aspect, bermekimab is administered by intravenous infusion over 60 minutes in each dose. In further aspect, bemekimab is administered between 5-10 mg/kg (e.g., about 7.5 mg/kg) intravenously, and 5-fluorouracil is administered between 2,000-2,400 mg/m$^2$, folinic acid is administered about 400 mg/m$^2$, and ONIVYDE is administered intravenously between 50-70 mg/m$^2$, this combination administered at a frequency of one time or once every other week.

In various embodiments, the inhibitor of the IL-1 pathway (for example XILONIX) is administered at any one or more of the dosages described herein at least once 1-7 times per week, 1-7 times per month, 5-10 times per month or combinations thereof for 1 month, 2 months, 3 months, 4 months, 5 months 6 months, 7 months, 8 months, 9 months, 10 months, 11 months, 12 months, 14 months, 16 months, 18 months, 20 months, 22 months, 24 months or combinations thereof. In some embodiments, XILONIX is administered at 4-8 mg/kg per month for 3-9 months. In some embodiments, XILONIX is administered at 5-8 mg/kg per month for 3-9 months. In some embodiments, XILONIX is administered at 6-8 mg/kg per month for 3-9 months. In some embodiments, XILONIX is administered at 7-8 mg/kg per month for 3-9 months. In some embodiments, XILONIX is administered at 4-8 mg/kg per month for 3-11 months.

Pharmaceutical Composition

In various embodiments, the present invention provides a pharmaceutical composition. The pharmaceutical composition includes an inhibitor of the IL-1 pathway (e.g, inhibitor of IL-1 and/or antagonist of IL-1R). In an embodiment, the inhibitor directly or indirectly inhibits IL-1α, IL-1β or IL-1R. In some embodiments, the inhibitor directly inhibits IL-1 receptor and is selected from the group consisting of a small molecule, a peptide, an antibody or a fragment thereof and a nucleic acid molecule. In some embodiments, the nucleic acid molecule is a siRNA molecule specific for IL-1 or IL-1R. In some embodiments, the antibody is selected from the group consisting of monoclonal antibody or fragment thereof, a polyclonal antibody or a fragment thereof, chimeric antibodies, humanized antibodies, human antibodies, and a single chain antibody. The pharmaceutical compositions according to the invention can contain any pharmaceutically acceptable excipient. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous. Examples of excipients include but are not limited to starches, sugars, microcrystalline cellulose, diluents, granulating agents, lubricants, binders, disintegrating agents, wetting agents, emulsifiers, coloring agents, release agents, coating agents, sweetening agents, flavoring agents, perfuming agents, preservatives, antioxidants, plasticizers, gelling agents, thickeners, hardeners, setting agents, suspending agents, surfactants, humectants, carriers, stabilizers, and combinations thereof.

In various embodiments, the pharmaceutical compositions according to the invention may be formulated for delivery via any route of administration. In one embodiment, the inhibitor of the IL-1 pathway is administered intravenously to the subject. "Route of administration" may refer to any administration pathway known in the art, including but not limited to aerosol, nasal, oral, transmucosal, transdermal, parenteral or enteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the parenteral route, the compositions may be in the form of solutions or suspensions for infusion or for injection. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Typically, the compositions are administered by injection. Methods for these administrations are known to one skilled in the art.

The pharmaceutical compositions according to the invention can contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins PA, USA) (2000).

Before administration to patients, formulants may be added to the inhibitor of IL-1/IL-1R. A liquid formulation may be preferred. For example, these formulants may include oils, polymers, vitamins, carbohydrates, amino acids, salts, buffers, albumin, surfactants, bulking agents or combinations thereof.

Carbohydrate formulants include sugar or sugar alcohols such as monosaccharides, disaccharides, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxethyl starch and carboxymethylcellulose, or combinations thereof "Sugar alcohol" is defined as a C4 to C8 hydrocarbon having an —OH group and includes galactitol, inositol, mannitol, xylitol, sorbitol, glycerol, and arabitol. These sugars or sugar alcohols mentioned above may be used individually or in combination. There is no fixed limit to amount used as long as the sugar or sugar alcohol is soluble in the aqueous preparation. In one embodiment, the sugar or sugar alcohol concentration is between 1.0 w/v % and 7.0 w/v %, more preferable between 2.0 and 6.0 w/v %.

Amino acids formulants include levorotary (L) forms of carnitine, arginine, and betaine; however, other amino acids may be added.

In some embodiments, polymers as formulants include polyvinylpyrrolidone (PVP) with an average molecular weight between 2,000 and 3,000, or polyethylene glycol (PEG) with an average molecular weight between 3,000 and 5,000.

It is also preferred to use a buffer in the composition to minimize pH changes in the solution before lyophilization or after reconstitution. Most any physiological buffer may be used including but not limited to citrate, phosphate, succinate, and glutamate buffers or combinations thereof. In some embodiments, the concentration is from 0.01 to 0.3 molar. Surfactants that can be added to the formulation are shown in EP Nos. 270,799 and 268,110.

Another drug delivery system for increasing circulatory half-life is the liposome. Methods of preparing liposome delivery systems are discussed in Gabizon et al., Cancer Research (1982) 42:4734; Cafiso, Biochem Biophys Acta (1981) 649:129; and Szoka, Ann Rev Biophys Eng (1980) 9:467. Other drug delivery systems are known in the art and are described in, e.g., Poznansky et al., DRUG DELIVERY SYSTEMS (R. L. Juliano, ed., Oxford, N.Y. 1980), pp. 253-315; M. L. Poznansky, Pharm Revs (1984) 36:277.

After the liquid pharmaceutical composition is prepared, it may be lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is administered to subjects using those methods that are known to those skilled in the art.

Kits

In various embodiments, the present invention provides a kit for treating or inhibiting cancer cachexia. The kit is an assemblage of materials or components, including a direct or indirect inhibitor of the IL-1 pathway IL-1/IL-1R. Thus in some embodiments, the kit contains (1) one or more of an inhibitor of IL-1α, an inhibitor of IL-1β, and an IL-1 receptor antagonist, (2) an instruction for use in being administered to a subject with cancer or cancer cachexia, and optionally (3) one or more chemotherapeutic agents and/or chemotherapy protective drug.

The exact nature of the components configured in the inventive kit depends on its intended purpose. In one embodiment, the kit is configured particularly for human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to treat or inhibit cancer cachexia in a subject. Optionally, the kit also contains other useful components, such as, measuring tools, diluents, buffers, pharmaceutically acceptable carriers, syringes or other useful paraphernalia as will be readily recognized by those of skill in the art.

The materials or components assembled in the kit can be provided to the practitioner stored in any convenient and suitable ways that preserve their operability and utility. For example, the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be a bottle used to contain suitable quantities of an inventive composition containing a direct or indirect inhibitor of IL-1, such as XILONIX. The packaging material generally has an external label which indicates the contents and/or purpose of the kit and/or its components.

Further embodiments provide the kit includes a device, e.g., a wearable biometric sensor, such that the subject is instructed to wear, before, during and/or after the treatment, a device that provides data to assess activity of the subject such as movement, altitude, heart rate, body composition, temperature, and sleep quality. For example, wearable activity monitors are provided to track the subject's physical activity before, after, or both before and after a disclosed treatment. Exemplary wearable sensors and/or monitors include pedometers, accelerometers, and multi-sensor systems, which detect or track functional status, prognosis and/or treatment tolerance by measuring parameters such as blood pressure, steps, metabolic equivalents, calories, or sleep.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1. Phase I Study of ONIVYDE and 5FU in Combination with XILONIX for Advanced Pancreatic Cancer Patients with Cachexia This study was aimed to examine the safety of the investigational drug, XILONIX™, in addition to standard doses of ONIVYDE® (nanoliposomal irinotecan) and 5-fluorouracil (5FU)/folinic acid (leucovorin) for pancreatic cancer patients with cachexia. Cachexia is a syndrome that includes involuntary weight loss and physical deterioration that can contribute to poor outcomes of cancer treatment. In other studies, XILONIX has increased lean body mass in advanced cancer patients. This increase could lead to improved weight maintenance and quality of life.

Main inclusion criterion was a diagnosis of advanced pancreatic cancer, who did not respond to an earlier treatment, with cachexia defined as 5% weight loss over a 6-month period of time.

This study prospectively evaluated advanced pancreatic adenocarcinoma patients. The intervention was interleukin-1-alpha antagonist (e.g., XILONIX) in addition to standard chemotherapy. The first aim was to assess the safety and identify the maximum tolerated dose of ONIVYDE with 5-fluorouracil/folinic acid in combination with the study agent, XILONIX, in a cohort of patients with advanced pancreatic adenocarcinoma and cachexia. The study also created a repository of serum, tissue, and fecal specimens to investigate novel biomarkers related to cachexia with pancreatic adenocarcinoma and interleukin-1-alpha blockade. Lastly, the study assessed for a correlation between cachexia, activity, and patient reported outcomes (PROs) on domains of quality of life.

The intervention would be successful when patients became able to maintain or gain weight and lean body mass. This will likely correlate with improved outcomes. In addition, we hypothesize that maintenance of weight would be associated with higher activity levels, and stable PROs around quality of life domains of fatigue, sleep, and general functioning. A weight stability in cachexia patients is weight change less than 0.1 kg/baseline BMI-unit. A positive study would support a randomized trial of interleukin-1-alpha antagonist (bermekimab/XILONIX) in addition to 5FU/FA and nanoliposomal irinotecan (ONIVYDE) in patients with advanced pancreatic cancer.

A secondary goal of this study was to better understand the unique mechanism of action IL6 antagonism and its relationships with pancreatic cancer anorexia-cachexia as well as with pancreatic cancer patients.

We would also investigate the role of key gut hormones known to regulate food intake in these patients. These hormones include glucagon-like peptide-1 (GLP-1), peptide YY (PYY), ghrelin, leptin and cholecystokinin (CCK). These hormones are contained in unique endocrine cell types in the gut epithelium and are released into the circulation with a meal. They play the key roles in regulating food intake through effects on both the GI tract and the CNS. Of note, GLP-1 and PYY are co-released from the same endocrine cell and are thought to play a key role in regulating food intake changes after gastric bypass surgery. Elevated serum levels GLP-1 has been found in patients with pancreatic cancer cachexia and we would confirm this finding in our cohort.

We would also further explore the impact of this therapy on quality life and patient reported outcomes in pancreatic cancer. We would utilize the EORTC QOL, and FACT-Hepatobiliary survey tools. They are both validated in patients with pancreatic cancer and will help us understand the benefit of this medication in our patient population. We would also assess pain using the Brief Pain Inventory, also validated in this population.

Currently, the majority of information upon which oncologists base their treatment decisions is obtained at the time of the patient clinic visit. This data includes the patient's recall of symptoms and physical functioning, in addition to laboratory, imaging and physical exam information. Patient reported data (PRD) can be affected by recall bias. Furthermore, PRD can be influenced by a patient's desire to affect the physician's understanding of their clinical condition. For example, patients may want their oncologist to believe that they are doing well, so that they may be a candidate for further cancer-directed therapies. Patient's may de-emphasize physical symptoms and tolerance to therapy in an attempt to convince themselves that they are doing well. Oncologists rely on the PRD to make their own clinical judgments regarding changes in a patient's clinical condition and therapy choices.

The utilization of wearable biometric sensors may allow an inexpensive method of acquiring objective clinical data. Currently, off-the-shelf technology is being used commercially to track fitness. These wrist-worn devices can provide real-time data relating to movement, altitude, heart rate, body composition, temperature, and sleep quality. We planned use a wrist-worn wearable biosensor to assess activity in patients with pancreatic cancer, and determine whether that activity correlates with changes in cachexia, functional status and PROs (i.e. EORTC QOL, and FACT-Hepatobiliary) around functional domains of quality of life. Data collected may support the efficacy of this therapeutic intervention and influence the development of additional patient-centric, meaningful endpoints for future therapeutic trials around cachexia.

Arms and Interventions

Interleukin-1-alpha antagonist (bermekimab, also known as XILONIX) in addition to standard chemotherapy of ONIVYDE and 5-fluorouracil and/folinic acid (leucovorin). XILONIX was administered via intravenous injection every 2 weeks. The duration of administration was every 2 weeks or according to investigator discretion, until patient stopped active therapy.

Approximately 6 months from screening to end of treatment assessment. Subjects continued to be followed for adverse events and survival for 36 months. In the treatment phase, each treatment cycle was about a month (or 28 days). Treatment on Day 1 and 15 of each cycle as per dosing schedule. Abbreviation C1, C3, C5 and C7, for example, refer to treatment cycle 1, 3, 5 and 7, respectively.

Primary Objective

To assess the safety and identify the maximum tolerated dose of ONIVYDE, 5-fluorouracil/folinic acid in combination with bermekimab (XILONIX) in a cohort of patients with advanced pancreatic adenocarcinoma and cachexia.

Secondary Objectives

To assess weight stability, defined as weight change less than 0.1 kg/baseline BMI-unit at 2 months from baseline;

To measure change in lean body mass by DXA at 2 months from baseline;

To measure changes in inflammatory cytokines, specifically interleukin-6, from baseline over 12-month study period;

To measure overall survival and progression free survival at 6 months and 12 months from baseline;

To evaluate relationship between treatment tolerance, QOL and patient functional status as measured using: 1) Wearable biometric sensor metrics (step count, stairs climbed, sleep duration, heart rate, active minutes) 2) ECOG/KPS performance status and 3) frailty (hand-grip, walk test);

Patient Reported Outcomes

To assess quality of life using EORTC Pan26 at 2, 4, and 6 months from baseline;

To assess patient-reported response to therapy using FAACT (Functional Assessment of Anorexia/Cachexia Therapy) at 2, 4, and 6 months from baseline;

Study Hypotheses Primary hypothesis is that ONIVYDE and 5FU/FA in combination with bermekimab (XILONIX)

in a cohort of patients with advanced pancreatic adenocarcinoma and cachexia is safe and tolerable.

Secondary hypotheses are that the treatment combination of ONIVYDE+5FU/FA+bermekimab (XILONIX) will maintain patient weight and lean body mass throughout treatment course; improve quality of life from baseline to end-of-study; increase levels of interleukin-6, which may predict overall benefit; improve symptoms of pain; improve progression-free survival and overall survival; this novel combination will improve the physical function of patients with pancreatic cancer and cachexia. Primary Outcome Measures
1. Number of Participants With Dose Limiting Toxicities (DLT) in the First Cycle for the determination of the Maximum Tolerated Dose (MTD) [Time Frame: 28 days (first cycle)] to assess safety of novel combination.
2. Maximum Tolerated Dose (MTD) of ONIVYDE, 5-fluorouracil/folinic acid in combination with XILONIX [Time Frame: 28 days (first cycle)] to assess MTD of ONIVYDE in combination with novel therapy.

Secondary Outcome Measures
1. Weight stability [Time Frame: 6 months] by measuring mean change from baseline (kg) up to 6 months.
2. Lean Body Mass [Time Frame: 6 months] by measuring mean change from baseline (kg) up to 6 months.
3. Overall Survival [Time Frame: 12 months] by measuring overall survival up to 12 months from baseline.
4. Progression Free Survival [Time Frame: 12 months] by measuring progression free survival up to 12 months from baseline.
5. Mean change in global quality of life (QOL) score (EORTC Pan26) [Time Frame: 6 months] by assessing patient-reported QOL up to 6 months from baseline.
6. Mean change in global score of patient-reported response to therapy (FAACT questionnaire-Functional Assessment of Anorexia/Cachexia Therapy) [Time Frame: 6 months] by assessing patient-reported outcomes up to 6 months from baseline.

Eligibility Criteria
Inclusion Criteria:
Advanced or locally advanced pancreatic cancer patients (can include new or recurrent diagnosis) referred to SOCCI-CSMC for chemotherapy that has progressed through or intolerant to gemcitabine based chemotherapy.

Cachexia defined as greater than 5% unexplained weight loss within any 6 months' period prior to screening visit or as documented by the medical physician based on standard diagnosis of cachexia.

Age ≥18 years.

ECOG performance status 0-2 or Karnofsky PS>60%.

Patients must have normal organ and marrow function as defined with: absolute neutrophil count (ANC)≥1,500/mcL, platelets≥100,000/mcL, total bilirubin<1.5 times upper limit of normal (ULN), AST(SGOT)/ALT(SGPT)≤2.5×ULN, and creatinine or creatinine clearance≤1.5 times the upper limit of normal or ≥45 mL/min/1.73 m² for patients with creatinine levels above normal.

Patients with biliary stents are eligible provided that all other inclusion criteria are met.

Negative pregnancy test in women of childbearing potential (WOCBP) within 30 days of study drug administration. WOCBP is a premenopausal woman capable of becoming pregnant. Rationale: The effects of this drug combination on the developing human fetus are unknown. Should a woman become pregnant or suspect she is pregnant while participating in this study, she should inform her treating physician immediately. Because there is an unknown but potential risk for adverse events in nursing infants secondary to treatment of the mother, breastfeeding should be discontinued if the mother is treated with the treatment combination under study. These potential risks may also apply to other agents used in this study.

WOCBP and men must agree to use of adequate contraception (hormonal or barrier method of birth control; abstinence) from the time of signing the informed consent form, for the duration of study participation, and for at least 30 days after discontinuing from study treatment.

Ability to understand and the willingness to sign a written informed consent. Exclusion Criteria:
Patients who are currently receiving any other investigational agents.

Patients who have received more than one chemotherapeutic regimen in metastatic setting.

Patients with CNS metastases.

Uncontrolled intercurrent illness including, but not limited to, ongoing or active infection, symptomatic congestive heart failure, unstable angina pectoris, cardiac arrhythmia, or psychiatric illness/social situations that would limit compliance with study requirements.

Patients with unresolved grade ¾ adverse effects of prior therapy at time of enrollment.

Subjects with history of hypersensitivity to compounds of similar chemical or biologic composition to XILONIX or ONIVYDE.

Women who are pregnant or breastfeeding.

Dementia or altered mental status that would prohibit the understanding or rendering of informed consent.

Patients with known Dihydropyrimidine dehydrogenase deficiency (DPD deficiency).

Patients known to be UGT1A1*28 allele homozygous.

Patients who have had a live vaccine within 3 months of enrollment.

Details
Primary Endpoint
To assess the safety (as assessed using CTCAE criteria graded and attributed by investigator) and identify the Maximum Tolerated Dose (MTD) of ONIVYDE in combination with novel therapy (number Dose Limiting Toxicities (DLT) in the First Cycle).

Secondary Endpoints
Weight stability (measured in kilograms) determined based on mean change from baseline to progression (measured every 2 months).

Lean body mass, as measured using DXA scan, determined based on mean change from baseline to progression (measured every 2 months).

Change in inflammatory cytokines to be determined based on mean change in research blood levels from baseline to progression (measured every 2 months). Research blood including: IL-6, interferon 1-alpha, TNF-alpha, Interleukin-10, neuropeptide y, ZAG, ghrelin, CCK, GLP-1, PYY, glucagon and insulin at baseline, and every 2 months until progression. We will use standardized ranges for normal levels of the following assays.

Progression free survival will be assessed by the principal investigator based on tumor biomarkers and RECIST 1.1 criteria during study period at baseline and every two months until progression. Measurements will be made based on standard scans conducted every 8 weeks per standard of care. Overall survival will be calculated from baseline to time of death.

Performance status will be recorded by the physician at baseline and at every clinic visit (Days 1 and 15) including end of study and follow-up visits.

Domains of quality of life and functional status including nutrition, food intake, frailty (measured using Fried's definition, 15-foot walk test, questionnaires, grip strength (measured via dynamometer during physical exam), QOL self-reported questionnaires (measured using EORTC PAN26, and FAACT), and activity (measured via daily collection of wrist-worn biometric sensor) will be determined based on mean change from baseline to progression (measured every 2 months).

Response to therapy would be assessed by the principal investigator based on tumor biomarkers and RECIST 1.1 criteria during study period. Measurements will be made based on standard scans conducted every 8 weeks per standard of care.

Survival would be evaluated at every visit and every 3 months during 36-month follow-up.

Research blood including: IL-6, interferon 1-alpha, TNF-alpha, Interleukin-10, neuropeptide y, ZAG, ghrelin, CCK, GLP-1, PYY, glucagon and insulin at baseline, 2, 4, and 6 months. Standardized ranges would be used for normal levels of the following assays.

Smell and taste alterations would be assessed by study staff using a validated survey at baseline and at 2, 4, and 6 months from baseline.

Food intake would be assessed by study staff at baseline at 2, 4, and 6 months from baseline. A validated 24-hour recall questionnaire would be analyzed using Food processor SQL version 10.12.

Presence of frailty phenotype using Fried's definition would be evaluated at baseline, and at 2, 4, and 6 months from baseline by measuring patient grip strength, using a dynamometer during physical exam, a 15 foot walk test, question about energy levels and activity.

Activity (steps taken, stairs climbed, sleep duration and disturbances, heart rate and intensity) would be collected using the wrist-worn biometric sensor daily for the duration of the study.

This phase I study was designed to identify the maximum tolerated dose (MTD) using four dose levels defined in Table 1. The MTD is defined as the dose such that the probability of DLT at the MTD is $\theta=0.33$. Escalation with overdose control (EWOC) algorithm would be used to design the trial. The first cohort of up to three patients would receive dose level −1 and the dose for the next cohort will be determined according to the EWOC algorithm. At any time during the trial, a patient might be enrolled to the trial if there are no more than two patients with unresolved DLT status in the trial. In other word, if there are three patients under treatment that did not experience DLT and have not finished their cycle 1 therapy, then another patient cannot be enrolled. The investigational treatment cycle is every 4 weeks. First post-treatment imaging and follow up will be performed 8 weeks after initiating therapy (C1D1). Patients removed from study for unacceptable adverse events will be followed until resolution or stabilization of the adverse event. Dose escalation schedule is provided in Table 1 (below) for each of the regimens being administered during the study.

TABLE 1

Dose escalation schedule.

| Dose Level | XILONIX IV[a] (mg/kg) | 5-Fluorouracil[b] (5FU) 2400 mg/m$^2$ | Folinic Acid[c] (Leucovorin) 400 mg/m$^2$ | ONIVYDE[d] IV 70 mg/m$^2$ |
|---|---|---|---|---|
| Level −1 | 7.5 mg/kg | 2000 mg/m$^2$ | 400 mg/m$^2$ | 50 mg/m$^2$ |
| Level 1 | 7.5 mg/kg | 2400 mg/m$^2$ | 400 mg/m$^2$ | 50 mg/m$^2$ |
| Level 2 | 7.5 mg/kg | 2400 mg/m$^2$ | 400 mg/m$^2$ | 70 mg/m$^2$ |
| Level −2 | 3.75 mg/kg | 2000 mg/m$^2$ | 400 mg/m$^2$ | 50 mg/m$^2$ |

[a]Selection of XILONIX dose based on the selected dose considered safe and tolerable from a recent Phase 1 study.
[b,c]Dose selection is based on standard doses for 5FU and FA (Leucovorin) as approved and recommended as part of standard of care.
[d]Dose selection for Nanoliposomal Irinotecan (ONIVYDE) based on FDA-approved recommended doses for advanced pancreatic cancer Bermekimab (XILONIX) will be administered per the dose escalation schema, see Table 1, beginning on day 1. Bermekimab (XILONIX) will be infused over 60 minutes. The starting dose of bermekimab (XILONIX) is 7.5 mg/kg IV every other week based upon safety/efficacy data available from the Investigator's Brochure. The second dose level will be 7.5 mg/kg IV every other week. There will be a de-escalation protocol to reduce the doses if there are unexpected dose limiting toxicities. In this trial, the minimum bermekimab (XILONIX) dose to be given is 3.75 mg/kg IV every other week.

Based on over 1200 doses of bermekimab (XILONIX) administered at 7.5 mg/kg, there have been no definite drug-related toxicities in patients with advanced cancer and cancer-associated symptoms (ECOG PS 1 and 2) at baseline. For purposes of safety reporting in clinical trials, the following events are considered expected: (1) Infusion-related reaction. There have been <1% of infusion reactions have been reported. (2) Injection site reactions.

The dose 3.75 mg/kg every 2 weeks was deemed to be the minimum effective dose in a dose escalation study, and the dose of 7.5 mg/kg was established in a large phase 3 trial.

ONIVYDE will be given at 50 mg/m$^2$ over 90 minutes on days 1, 15 (Level 1, Level −1) and a maximum of 70 mg/m$^2$ (Level 2). Details on administration and preparation are available in the pharmacy manual and/or package insert. Common side effects of ONIVYDE include: (1) severe neutropenia—fatal neutropenic sepsis occurred in 0.8% of patients receiving ONIVYDE. Severe or life-threatening neutropenic fever or sepsis occurred in 3% and severe or life-threatening neutropenia occurred in 20% of patients receiving ONIVYDE in combination with Fluorouracil and Leucovorin. (2) Severe diarrhea: Severe diarrhea occurred in 13% of patients receiving ONIVYDE in combination with Fluorouracil and Leucovorin. Should not be administered in patients with bowel obstruction. ONIVYDE should be withheld in patients with diarrhea of grade 2-4 severity. Patients who have grade 2 diarrhea at baseline will not be medically eligible.

5FU will be administered as per standard of care. 5FU will be administered by intravenous infusion as per the dosing schedule outlined in Table 1 over 46 hours on days 1, 15 of the cycle. Details on administration and preparation of 5FU are provided in the pharmacy manual and/or package insert.

Leucovorin (folinic acid) will be administered as per standard of care. Details on administration and preparation of Leucovorin are available in the pharmacy manual and/or package insert.

Subjects will be premediated with standard corticosteroids and an antiemetic 30 minutes prior to ONIVYDE administration, per package insert. Supportive medications will be prescribed for nausea/vomiting/diarrhea, as clinically indicated.

To date, there are no anticipated drug interactions between bermekimab (XILONIX) and ONIVYDE in combination with 5FU/FA. Bermekimab (XILONIX) has not been shown to interact with any other concomitant medications. ONIVYDE is known to interact with CY3A4 inducers (e.g., rifampin, phenytoin, carbamazepine, rifabutin, rifapentine, phenobarbital, St John's wort); CY3A4 inhibitors (e.g., clarithromycin, indinavir, itraconazole, lopinavir, nefazodone, nelfinavir, ritonavir, saquinavir, telaprevir, voriconazole) or UGT1A2/1 (e.g., atazanafir, gemfibrozil, indinavir). Patients on strong CYP3A4 inhibitors should discontinue at least one week prior to starting ONIVYDE. Subjects should avoid the use of strong UGT1A1 and UGT1A2 inhibitors, if possible.

Treatment is administered according to the schedule (Table 1). Treatment will be delivered over 4 weeks (1 cycle=28 days). Patients will be evaluated for DLT during the first treatment cycle. Doses can be delayed or modified in the event of an adverse event or at the physician's discretion. Thus, adverse events will be collected and reviewed at every patient visit. If doses are delayed, patients will be evaluated for DLT within two weeks after the second dose. If there is more than a three-week delay between the first and second dose, (both doses must be received within four weeks) the patient is not evaluable (but they will continue to follow the protocol-directed procedures).

To appropriately assess toxicity and possible dose limiting toxicities during treatment, patients will be seen in clinic by a practitioner every 2 weeks, or per investigator's discretion, with blood work drawn as per the study calendar. Therapy may be administered provided that the patient has no evidence of progressive disease and meets criteria for treatment as defined in Section 4.3 "Dose Modifications." As this design uses the EWOC design, dose modifications and schedule will be determined by the biostatistician or the biostatistical support will be provided for the duration of the dose-finding study Toxicity will be evaluated using the NCI Common Terminology Criteria for Adverse Events, Version 4.0. The frequency of toxicities per organ system will be tabulated using descriptive statistics. All patients who receive any amount of the study drug will be evaluable for toxicity.

After the dose-limiting toxicity (DLT) period is complete, dosing modifications, timing, and combination is per investigator discretion.

The evaluable DLT period is within two weeks after patients' second dose (irrespective of when it was given). DLTs are any of the below that are suspected to be related or possibly related to any one of the drugs in combination. If a patient experiences a DLT, treatment to be held. Treatment to resume per investigator discretion.

Grade=4 thrombocytopenia or anemia
Grade 3 thrombocytopenia associated with bleeding
Grade ≥3 febrile neutropenia
ANC <100 mcL for ≥3 days
ANC <500 mcL for ≥5 days
Any non-hematologic grade ≥3 will be dose-limiting with the exception of Grade 3 nausea, vomiting, and diarrhea that resolves within 5 days
Any Grade 4 toxicity The toxicity assessment of the phase 1 portion will be 1 treatment cycle over 28 days. Then patients will continue until disease progression or until any of the following occur:

Inter-current illness that prevents further administration of treatment

Unacceptable adverse event(s)
Experiencing DLT(s), which in the opinion of the PI precludes resuming treatment with dose reduction due to unfavorable risk-benefit ratio (for the first 28-day cycle)
Patient decides to withdraw from the study, OR
General or specific changes in the patient's condition render the patient unacceptable for further treatment in the judgment of the investigator.

In the absence of the above criteria, subjects may continue to receive study treatment at the investigator's discretion.

Patients will undergo an End of Treatment assessment 30 days after removal from treatment. Patients removed from treatment for unacceptable adverse events will then be followed until resolution or stabilization of the adverse event and will continue to be followed for the duration of the study as per protocol. After the End of Treatment Assessment, follow-up will involve every 3-month phone calls to collect survival data for 36 months.

Subjects who withdraw from the study treatment prior to starting the study intervention may need to be replaced at the discretion of the study PI. Furthermore, subjects who do not complete the DLT stage of the study intervention will also be replaced at the discretion of the study PI in order to be evaluable for the primary endpoint.

Operating Characteristics

For the purpose of deriving the operating characteristics of the study, it is assumed that successive cohorts of two patients will be treated and the dose for the first cohort of two patients will be level-1. The dose for each subsequent cohort of two patients will be determined so that, based on all available data, the probability that it exceeds the MTD is equal to a prespecified value $\alpha$. In this trial, we start at $\alpha=0.3$ and increase a in small increments of 0.05 until $\alpha=0.5$, this value being a compromise between the therapeutic aspect of the agent and its toxic side effects. No dose skipping will be permitted. The trial will be terminated if the posterior probability that the probability that DLT at dose level-2 exceeds $\theta$ is 0.8 or more. Further, flexibility is added to introduce dose level-3 in the trial (increase dose of ONIVYDE only and keep the dose level of the other three drugs the same as dose level-2) if there is statistical evidence that the probability that the posterior probability of DLT at dose level 2 is too low is high. Specifically, if $P(P(DLT|dose=level\ 2)<\theta-0.1|data)>0.8$, then an additional dose level is introduced.

Study Procedures:
Screening/Baseline Procedures

Assessments performed exclusively to determine eligibility for this study will be done only after obtaining informed consent. Assessments performed for clinical indications (not exclusively to determine study eligibility) may be used for baseline values even if the studies were done before informed consent was obtained.

All screening procedures must be performed within 4 weeks of Day 1 unless otherwise stated. Baseline visit can also occur on Cycle 1, Day 1 of treatment. The screening procedures include:

Informed Consent must be obtained within 6 weeks of Day 1 5.1.2
Review subject eligibility criteria
Medical history: Complete medical and surgical history, history of infections
Demographics: Age, gender, race, ethnicity
Review previous and concomitant medications Physical exam including vital signs, height and weight:
Vital signs (temperature, pulse, respirations, blood pressure), height, weight, hand grip strength Performance status: Performance status evaluated prior to study entry according to eastern cooperative group (ECOG) criteria Adverse event assessment: Baseline adverse events will be assessed from C1D1 for the duration of the study. See Section 6 for Adverse Event monitoring and reporting Blood collection for general health assessment: CBC with differential, CMP, Phosphorus, Magnesium Blood draw for research studies Blood draw for tumor assessment: CA-19-9 will be assessed Stool sample: A stool collection kit will be given to the patient during physical exam, where patient will be advised to follow instructions on kit and bring their sample into laboratory +/−7 days of screening/baseline visit. Microbiome analysis will be measured from collection of stool sample Research Tissue biopsy: These samples will be used to determine the levels of different DNA repair proteins, including PAR, XRCC1, BRCA1, BRCA2, etc.) and assess BRCA1/2, PTEN, PALB2, P16 mutational status Patient reported outcomes: Patient reported outcomes (EORTC PAN26; FAACT)

Activity monitoring: Biosensor activity monitoring to measure step count, heart rate, activity intensity, stairs climbed and sleep. Provide wearable biosensor with charger and instructions.

Pregnancy test for women of child-bearing potential as per standard of care.

DXA Scan: Must be conducted prior to CT imaging or 10-14 days after CTs with contrast. IV and oral contrast cause an artifact in DxA images that affects assessment of lean body mass. Acceptable to have done after receiving treatment.

Procedures During Treatment: These visits can occur within a window of −/+3 business days of the anticipated visit date to account for clinic closures or holidays Every Cycle (each 4 weeks/28 days)
  Day 1:
    Safety evaluation (as per CTCAE version 4.03)
    Physical Exam
    Weight
    Vital signs
    ECOG performance status (Appendix A)
    Concomitant medications
    Blood collection (CBC, CMP, Phos, Mag)
    Assess wearable biosensor functionality
    Treatment as per dosing schedule
  Day 15:
    Safety evaluation (As per CTCAE grading)
    Physical Exam
    Weight
    Vital signs
    ECOG performance status (Appendix A)
    Concomitant medications
    Blood collection (CBC, CMP, Phos, Mag)
    Treatment as per dosing schedule
Every Other Cycle (Every 8 weeks)
  Day 1 (Clinic Visit) (+/−3 days)
    Treatment as per dosing schedule
    Safety evaluation (As per CTCAE version 4.03)
    Physical Exam
    Weight
    Vital signs
    ECOG performance status
    Concomitant medications
    Blood collection (CBC, CMP, Phos, Mag)
    Tumor markers (CA 19-9)
    CRP
    Research blood (See Section 7)
    QOL surveys: PAN26, FAACT
    Frailty status (hand grip; 15 ft walk-test; activity questionnaire)
    Assess wearable biosensor functionality
    DXA scan (On Cycle 3, Day 1 ONLY, +/−7 days)
      Must be conducted prior to CT imaging or 10-14 days after CTs with contrast. IV and oral contrast cause an artifact in DxA images that affects assessment of lean body mass. Acceptable to have done after receiving treatment.
    CT imaging/scan: Evaluation of tumor response (Every 8 weeks as per standard of care, +/−7 days)
    Bionutrition assessment (24-hour recall+taste and smell alteration) conducted by study staff (+/−14 days)
    Stool sample collection—Microbiome analysis (Section 9) (On Cycle 1, Day 1 and Cycle 3, Day 1 ONLY, +/−7 days))
  Day 15:
    Safety evaluation (As per CTC AE grading)
    Physical Exam
    Weight
    Vital signs
    ECOG performance status
    Concomitant medications
    Blood collection (CBC, CMP, Phos, Mag)
    Treatment as per dosing schedule
End of Study Visit procedures:
  30 days after treatment termination (+/−7 days)
    Safety evaluation (As per CTC AE grading)
    Physical Exam
    Weight
    Vital signs
    ECOG performance status
    Concomitant medications
    Blood collection (CBC, CMP, Phos, Mag)
    Tumor markers (CA 19-9)
    CRP
    Research blood
    QOL surveys: PAN26, FAACT
    Frailty status (hand grip; 15 ft walk-test; activity questionnaire)
    End of wearable biosensor physical activity assessment
    Continue treatment at physician's discretion 5.4 Follow-up Procedures Patients will be followed every 3 months for 36 months after EOS visit/completion of (or early withdrawal from) study treatment or until death. The following will be assessed during follow-up:
  ECOG performance status
  Medical chart review for survival and adverse events. If no records of patient survival in medical chart, PI or study staff may call to assess survival and adverse events.

Time and Events table, Table 2:

| Procedures | Screening/ Baseline All to occur within 28 days prior to Cycle 1, Day 1 | Treatment Phase until progression | | | | End of Study 30 days after study termination (+/− 7 days) | Follow-up Phase Survival Follow-up Every 3 months for 36 months (+/− 7 days) |
|---|---|---|---|---|---|---|---|
| | | Every Cycle (Every 4 weeks) Repeats every cycle | | Every other Cycle (Every 8 weeks) Repeats every other cycle | | | |
| | | Day 1 (+/− 3 days)[1] | Day 15 (+/− 3 days)[1] | Day 1 (+/− 3 days)[1] | Day 15 (+/− 3 days)[1] | | |
| Informed Consent* | X | | | | | | |
| Eligibility review | X | | | | | | |
| Pregnancy test | X | | | | | | |
| Demographics | X | | | | | | |
| Medical/Surgical History | X | | | | | | |
| Complete Physical Exam | X | X | X | | | X | X |
| Height | X | | | | | | |
| Weight | X | X | X | | | X | |
| Vital Signs | X | X | X | | | X | |
| Performance Status (ECOG) | X | X | X | | | X | |
| Adverse Event Assessment | | X[8] | X | | | X | |
| Concomitant Medications | X | X | X | | | X | |
| Tumor assessment (imaging) | X | | | X[9] | | X | |
| Blood collection (CBC, CMP, Phos, Mag) | X | X | X | | | X | |
| CA 19-9 (biomarker) | X | | | X | | X | |
| C-reactive protein (CRP) | | | | X | | X | |
| Research Blood Tests[1] | | | | X | | | |
| Stool Sample[2] | X | | | X | | | |
| Tissue biopsy (Optional) | X | | | | | | |
| Hand grip and 15 ft walk test[3] | | | | X | | X | |
| DXA scan[4] | X | | | X | | | |
| Bionutrition assessment: 24-hour food recall; taste and smell alteration[12] | | | | X | | | |
| QOL survey: PAN26; FAACT[10] | X | | | X | | X | |
| Physical Activity: Assess Fitbit functionality[5] | X | X | | | | X | |
| Bermekimab (XILONIX)[6,7] | | X | X | | | | |
| ONIVYDE[6,7] and pre-meds 30 minutes prior to administration | | X | X | | | | |
| 5FU[6,7] | | X | X | | | | |
| Leucovorin[6,7] | | X | X | | | | |
| Survival Follow-up | | | | | | | X |

*Informed consent can be signed within 6 weeks of study initiation
[1]Research blood tests include: IL-6, interferon 1-alpha, TNF-alpha, Interleukin-1ß, neuropeptide y, ZAG, ghrelin, CCK, GLP-1, PYY, glucagon and insulin
[2]Stool kit will be provided to patients at study visit where patients will be asked to follow the instructions and return the stool sample to CSMC within the specified timeframe at screening/baseline (+/− 7 days), Cycle 1, Day 1, and Cycle 3, Day 1 ONLY.
[3]Hand-grip using the hand-held dynamometer. Three assessments for each hand will be completed and recorded. A timed walk-test from first foot fall to last foot fall over 15 feet will be performed twice per assessment. Assessments will be used to evaluate frailty status as per Fried's definition. This will be done at Day 1 of every odd cycle.
[4]DXA will be evaluated by study staff (coordinator or other trained staff) at baseline and Day 1 of Cycle 3 ONLY (+/− 7 days)
[5]Wearable biosensor will be provided at time of informed consent. Patients are asked to wear the biosensor continuously over the entire treatment period. Data collected includes steps, stairs climbed, heart rate, active minutes, and sleep. Biosensor functionality will be assessed once per cycle to ensure proper syncing.
[6]Dose as assigned; see administration schedule. Dosing schedule may be modified based on investigator discretion
[7]Patients who show benefit from treatment can continue, even after completion of study.
[8]Assessment for dose-limiting toxicities (DLT) occurs at each clinic visit for the first cycle only (28 days). If patient continues treatment after the first cycle, the attending oncologist will proceed with standard assessment of adverse events.
[9]At Baseline and every 8 weeks from C1D1 as per standard of care ((+/− 7 business days).
[10]Self-administered for English speaking patients. For non-English speaking patients, an interpreter will translate.
[11]Business days.
[12]+/− 14 days.

Removal of Subjects from Study

Patients can be taken off the study treatment and/or study at any time at their own request, or they may be withdrawn at the discretion of the investigator for safety, behavioral or administrative reasons. The reason(s) for discontinuation will be documented and may include: Patient voluntarily withdraws from treatment (follow-up permitted); Patient withdraws consent (termination of treatment and follow-up); Patient is unable to comply with protocol requirements; Patient experiences toxicity that makes continuation in the protocol unsafe; Treating physician judges continuation on the study would not be in the patient's best interest; Patient becomes pregnant (pregnancy to be reported along same timelines as a serious adverse event); Lost to follow-up. If a research subject cannot be located to document survival after a period of 2 years, the subject may be considered "lost to follow-up." All reasonable efforts must be made to locate subjects to determine and report their ongoing status. Lost to follow-up is defined by the inability to reach the subject after a minimum of three documented phone calls, faxes, or emails as well as lack of response by subject to one registered mail letter; or any combination of the above.

All attempts should be documented in the subject's medical records. If it is determined that the subject has died, the site will use permissible local methods to obtain the date and cause of death. If after all attempts, the subject remains lost to follow-up, then the last known alive date as determined by the investigator should be reported and documented in the subject's medical records.

Correlatives/Research Studies

Research Blood Collection Kit and Instructions. This Kit is for collection, processing, storage and/or shipping of serum, plasma, or whole blood (as specified by the protocol). Kit contents:
- One (1) 5-10 cc Red Top tube for serum (A)
- One (1) 5-10 cc Lavender Top EDTA preserved with anticoagulant tube for plasma (B)
- One (1) 5-10 cc Lavender Top EDTA preserved with anticoagulant tube for Whole Blood (C)
- Fifteen (15) to thirty (30) 1 ml cryovials
- Pipettes
- Two (2) patient-specific cryovial storage boxes
- Biohazard bags (3) and Absorbent shipping material (3)
- Styrofoam container (inner) and Cardboard shipping (outer) box
- UN1845 DRY Ice Sticker and UN3373 Biological Substance Category B Stickers
- Lab Requisition Form and Kit Instructions Preparation and processing of serum, plasma and whole blood:

Serum: Red Top Tube
  Label as many 1 ml cryovials (up to 5-10) as necessary for the serum collected. Label them with:
  Study name: OnX
  Patient initials (First, Middle, Last)
  Collection date (Month, Day, Year)
  Serum cryovial number (e.g., 51, S2, S3, S4, S5, etc. . . . )
Process
  Transport Red Top Tube for processing at room temperature
  Allow the blood to clot by leaving it undisturbed at room temperature (15-30 minutes)
  Centrifuge at 1,000×g for 10 minutes in a refrigerated centrifuge (4° C.). If unable to process samples at 4° C. then spinning at room temperature is acceptable if done within 2 hours of draw but must be noted on the Lab Requisition Form.
  Aliquot 0.5 ml serum into as many 1 ml cryovials (up to 5-10) as are necessary for the serum collected and stored at −80° C. Ensure the patient initials, collection date and serum cryovial number (e.g., S1, S2, S3, S4, S5, etc. . . . ) are marked on the cryovials.
  Place cryovials into the patient-specific cryovial storage box and immediately freeze at −70 to −90° C., and store frozen until ready to ship/transfer. See below for storage conditions.
Plasma: Lavender Top EDTA Tube #1
  Label as many 1 ml cryovials (up to 5-10) as necessary for the plasma collected. Label them with:
  Study name: OnFX
  Patient initials (First, Middle, Last)
  Collection date (Month, Day, Year)
  Plasma cryovial number (e.g., P1, P2, P3, P4, P5, etc. . . . )
Process
  After collection, invert tube(s) twice to ensure adequate mixing of EDTA.
  Centrifuge specimen(s) within one hour of collection at 2,000×g for 15 minutes in a refrigerated centrifuge (4° C.). If unable to process samples at 4° C. then spinning at room temperature is acceptable if done within 2 hours of draw but must be noted on the
  Lab Requisition Form.
    If the interval between specimen collection and processing is anticipated to be more than one hour, keep specimen on ice until centrifuging is performed.
    Aliquot 0.5 ml plasma into as many 1 ml cryovials (up to 5-10) as are necessary for the plasma collected and stored at −80° C. Ensure the patient initials, collection date and plasma cryovial number (e.g., P1, P2, P3, P4, P5, etc. . . . ) are marked on the cryovials.
    Place cryovials into the patient-specific cryovial storage box and immediately freeze at −70 to −90° C., and store frozen until ready to ship/transfer. See below for storage conditions.
Whole Blood: Lavender Top EDTA Tube #2
  Label as many 1 ml cryovials (up to 5-10) as necessary for the whole blood collected. Label them with:
  Study name: OnFX
  Patient initials (First, Middle, Last)
  Collection date (Month, Day, Year)
  Whole blood cryovial number (e.g., WB1, WB2, WB3, WB4, WB5, etc. . . . )
Process
  After collection, invert tube(s) twice to ensure adequate mixing of EDTA.
  Blood can also be mixed for 5 minutes on a mixer at room temperature.
  Aliquot 0.5 ml blood into as many 1 ml cryovials (up to 5-10) as are necessary for the whole blood collected and stored at −80° C. Ensure the patient initials, collection date and whole blood cryovial number (e.g., WB1, WB2, WB3, WB4, WB5, etc. . . . ) are marked on the cryovials.
  Place cryovials into biohazard bag and immediately freeze at −70 to −90° C., and store frozen until ready to ship/transfer. See below for storage conditions.
All Blood Samples—Freezing and Storage:
  Freeze all blood samples in a −80° C. Freezer or on Dry Ice or snap freeze in liquid nitrogen.
  Store at −80° C. (−70° C. to −90° C.) until ready to transfer.
  If a −80° C. Freezer is not available,
  Samples can be stored short term in a −20° C. freezer (non-frost free preferred) for up to one week; OR
  Samples can be stored in plenty of dry ice for up to one week, replenishing daily; OR
  Samples can be stored in liquid nitrogen vapor phase
  Please indicate on Lab Requisition the storage conditions used and time stored.
  Optional Research Biopsy
Collection of Specimen(s)
  If patient consents to the optional tissue biopsy, tissue will be obtained (EGD or CT-guided) from fine needle aspiration using either a 19-22 gauge or 25 gauge needle. Alternatively, tissue will be obtained via core biopsy using a 19-22 gauge needle.

Approximately 2-4 passes will be made until adequate specimen is obtained. 0.5 g tumor tissue will be obtained for PCR-based gene sequencing of pancreatic tumors for somatic BRCA1/2 mutational analysis and expression assessment.

Handling of Specimens(s)

Half of the specimen will be snap frozen in liquid nitrogen within 30 minutes of performing biopsy to minimize tissue anoxia; specimen will be frozen long-term at −80 degrees Celsius in cryovials. The remaining specimen will be fixed in 4% paraformaldehyde. Samples will be stored indefinitely in Dr. Bhowmik's CSMC laboratory unless the patient withdraws consent.

Analysis of Specimen(s)

Frozen tissue specimen will be processed for DNA/protein extraction and isolation; formalin-fixed tissues will be paraffin embedded and sectioned. DNA damage repair proteins will be quantitated using Western, ELISA and immunohistochemistry.

Collection Kit and Instructions
  Kit contents:
  Supply of 1 ml cryovials
  Disposable Scalpels
  Portable LN canister
  Tongs (for removal of cryovial from canister)
  Cryovial storage boxes
  Gloves for handling cold items
  Labeling Instructions for all Research Tissue:
  Label as many containers as necessary for collection.
    Label them with:
    Study name: OnFX
    Patient initials (First, Middle, Last)
    Patient ID # (PI Last name, IRB #, Patient #): Hendifar, IRB #46855, TBD
    Collection date (Month, Day, Year)
    Snap frozen cryovial number (e.g., SF1, SF2, SF3, SF4, SF5, etc. . . . ) or Fixed tissue number (e.g., FT1, FT2, FT3, FT4, FT5, etc. . . . )
  Snap Freezing
  Minimum size of tissue for snap freezing is approximately 0.5 cm3, though the amount of tissue available will differ depending upon the sample
  Place samples directly into cryovial
  Flash freeze in canister of LN2
  If there is sufficient material, freeze duplicate samples
  Transfer samples for long term storage to −80° C. Freezer
  Fixation & Tissue Processing Protocol
  Fixative: Freshly made RNase-free 4% paraformaldehyde (4% PF) used specifically for In Situ Hybridization; 4% paraformaldehyde or 10% buffered formalin used for routine histology (i.e., H&E staining, IHC, etc.)
  Fixation Procedure: the following protocols are for tissue sample processing for subsequent light microscopy with H&E staining, immunocytochemistry or in situ hybridization. RNase-free PBS and fixative should be used for in situ hybridization with RNA probes.
  Use the 60 ml yellow-capped containers with 30-40 ml solution volumes or 20 ml scintillation vials with 15-20 ml solution volumes to fix, wash and dehydrate the samples.
  Well-fixed samples can be stored in the same fixative at 4° C. for several days or even longer for H&E staining. In situ hybridization samples must be dehydrated and stored at −20° C. with 100% ethanol after 24-48 hours fixation. Immunohistochemistry samples must be dehydrated and stored at −20 degrees Celsius with 100% ethanol after overnight fixation.

Tissue Fixation
1. Isolate the tissue into cold PBS as soon as possible.
2. Wash tissue with PBS to remove all blood.
3. Place tissue in fixative for 10-15 minutes to one hour.
4. Cut tissue to proper size. The size can be 2×2 mm to 1×2 cm but thickness must be thinner than 3 mm for better fixation. The cutting surface of the tissue should be flat and smooth.
5. Transfer tissue to fixative and swirl the container to ensure all tissues are completely immersed in fixative. The volume of fixative must be 20-30 times the tissue volume.
6. Fix tissue at 4° C. for overnight.
7. Check sample the next day to ensure proper fixation.

Tissue Processing

The following wash and dehydration steps should be carried out at 4° C. on a shaker (No shaking with E8.5-9.5 embryos). Use RNase-free solutions for in situ hybridization.
1. Wash with PBS 1 min.
2. Wash with PBS 30 min X4.
3. Dehydrate:
   30% ethanol in ddH$_2$O for 2 hours.
   50% ethanol in ddH$_2$O for 2 hours.
   70% ethanol in ddH$_2$O for 4 hours or O/N.
   95% ethanol for 3 hours×2 or O/N.
   100% ethanol for 1 hour×2.
   Store at −20° C.
   100% ethanol for 1 hour×3 at RT.
4. Xylene 30-40 min×2, Check embryos.
5. Paraffin 40 min×3.
6. Embedding. Store at 4° C.

Fecal Specimen Collection

Materials: Microbial Collection and Stabilization kit: OMNIgene•GUT–DNA Genotek Protocol for frailty criteria*:

D1. Weight loss: Weigh patient and assess for weight loss. Someone who is frail may have unintentional weight loss of ≥10 pounds in the prior year.

D2. Gait speed: Time a patient's walk for slowness. Someone who is frail has a decreased walking time as defined by a timed 15-foot walk test (5 meters). The time is adjusted for gender and standing height. Men with a height of <173 cm and women with a height <159 cm who walked 15 feet in >7 sec are considered frail; men >173 cm and women >159 cm who walked 15 feet in >6 sec are considered frail.

D3. Weakness: Weakness is established when there is decreased grip strength measured by a dynamometer with the value adjusted for gender and body mass index (BMI). Men with a BMI <24 are considered frail if the grip strength (kg) is <29, for a BMI of 24.1-28, a man is frail if <30, for a BMI >28 a man is frail if <32. For women, a BMI of <23 is considered frail if the grip strength (kg) is <17, a BMI 23.1-26 is considered frail if <17.3, a BMI of 26.1-29 is considered frail if <18, and a BMI >29 is considered frail if <21.

D4. Physical Activity: Determine if the patient has a low physical activity level. This is established by a weighted score of kilocalories expended per week measured by the Minnesota Leisure Time Activity Questionnaire. The questionnaire asks about activities like daily living, sports and hobbies. Frailty is present when males use <383 kcal/week, and females <270 kcal/week.

D5. Frailty Phenotype: Score will be calculated based on presence of each of these characteristics where presence of 1-2 criteria are categorized as prefrail, and >=3 criteria categorized as frail.

Example 2. Initial Analysis of the Phase One Study in Example 1

Eight enrolled patients had a median age of 67 years (range 55-79), 3 women, all with advanced pancreatic cancer and cachexia. Their races were as follows: 3 Caucasian, 3 Asian and 2 African American. Of the 8 patients 6 were evaluable, as summarized in table 2.

TABLE 2

Clinical Features of Enrolled Patients

| | |
|---|---|
| # of Enrolled Patients | 8 |
| # of Evaluable Patients | 6 |
| Median Age | 67 years |
| Sex | Female: 3 |
| | Male: 5 |
| Race | Caucasian: 3 |
| | Asian: 3 |
| | African American: 2 |

Figure 2:
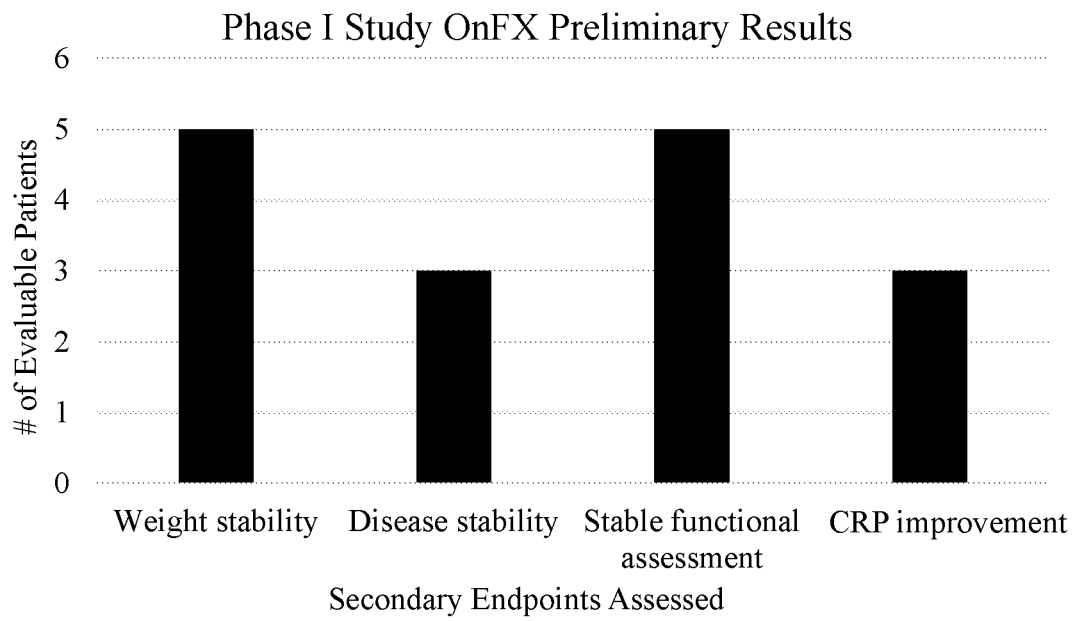
FIG. 2 is a bar graph showing the number of patients having weight stability, disease stability, stable functional assessment, or CRP elevation, at the secondary endpoints in the phase one study described in Example 1.

There was only 1 dose limiting toxicity for grade 3 fatigue. 3/6 had disease stability including 1 partial response. 5/6 had weight stability, 5/6 has stable functional assessment based on the frailty score. C-reactive protein (CRP) was significantly elevated in 3/6 patients and improved with treatment. (FIGS. 1 and 2).

The addition of interleukin-1-alpha-antagonist therapy to nano-liposomal irinotecan and 5-fluorouracil was well tolerated at least up to the time this patent application is filed with 1 dose limiting toxicity over more than 25 treatments. Activity was promising and better than expected for a cohort of refractory patients with significant weight loss. Patients were also able to retain lean body mass and functional status. These data supported further development of this chemotherapy combination in advanced pancreatic cancer patients with weight loss.

Example 3. Second Set of Data from OnFx Clinical Trial in Example 1

18 patients were enrolled, of which 15 were evaluable. Subject IDs (SIDs) 1-18, wherein SIDs 2, 4 and 11 were not evaluable. Data was collected at treatment cycles C1, C3, C5, C7, etc. Each treatment cycle was about 28 days.

The percentage of patients showing positive response to the treatment of pancreatic cancer was 27%, whereas 67% of the patients had stable disease (SD) and 7% of the patients had disease progression (PD).

The percentage of patients showing weight stability (measured after 2 cycles, or two months) was 53%, calculated as weight decrease of less than 0.1 kg/BMI or any increase. 47% of the patients experienced unstable weight, calculated as weight decrease of 0.1 kg/BMI or greater. BMI stands for body mass index (kg/m$^2$).

Figure 3:
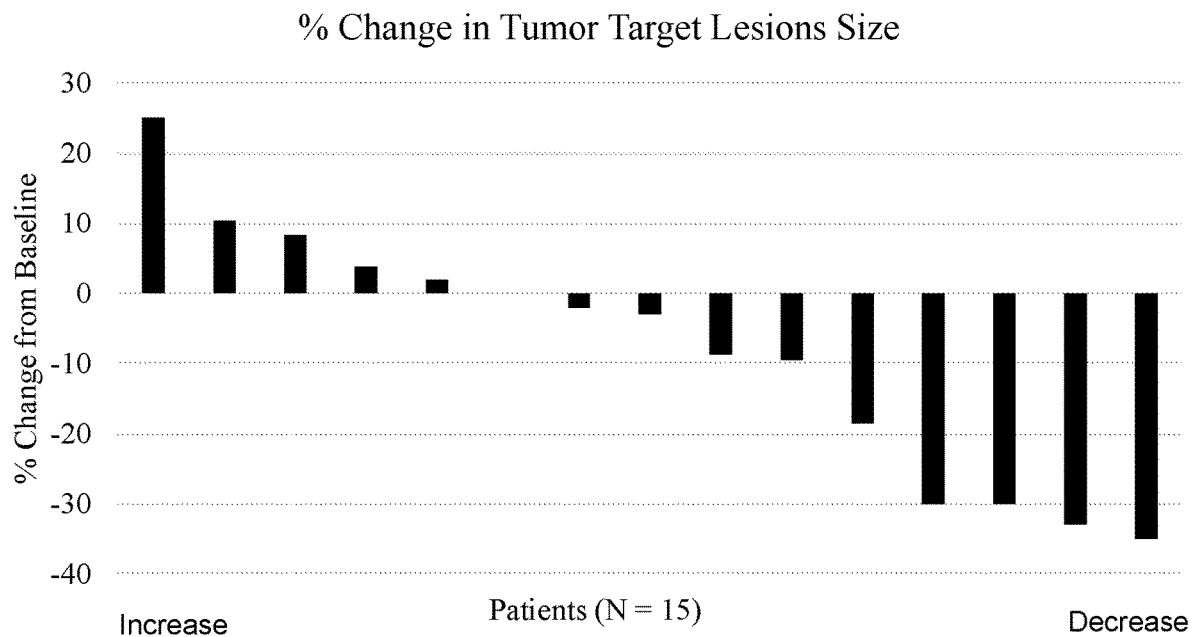
FIG. 3 depicts the percentage change in the tumor target lesions size of each patient (N=15) in the study in Example 1.

FIG. 3 shows the percentage of change in tumor target lesion size, compared to baseline, of each of the 15 evaluable patients.

Figure 4A:
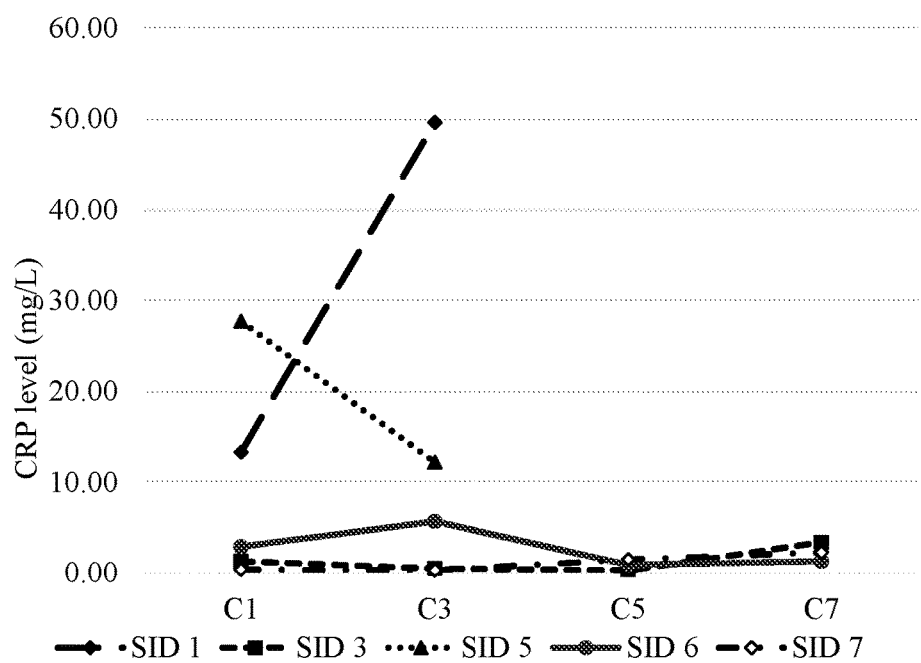
FIGS. 4A-4C depict the levels of C-reactive protein (CRP) (mg/L) of each subject at the end of different treatment cycles (cycle 1, C1; cycle 3, C3; cycle 5, C5; and/or cycle 7, C7).
Figure 4B:
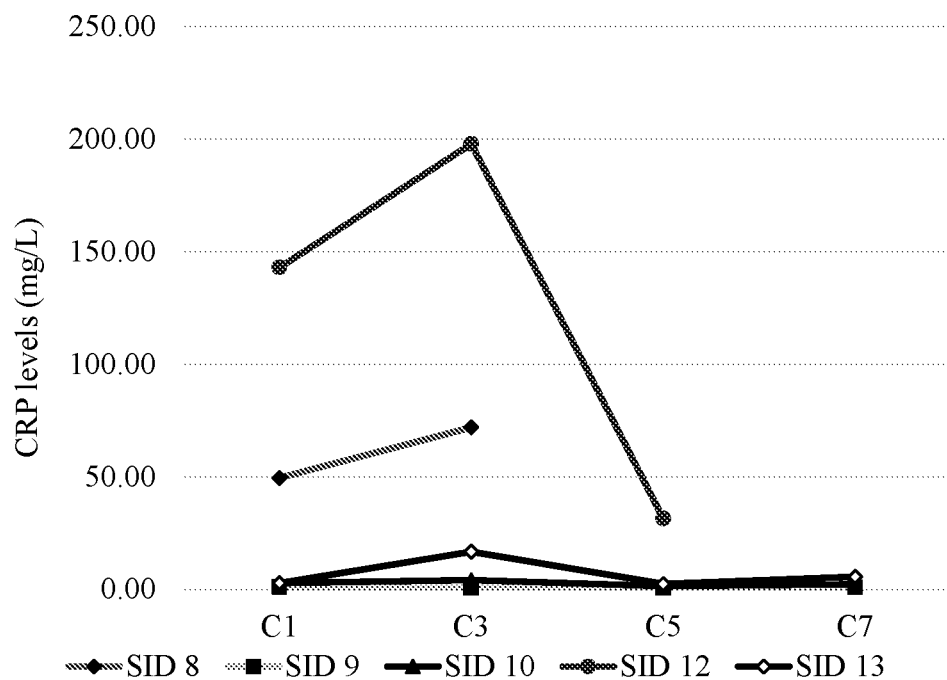
Figure 4C:
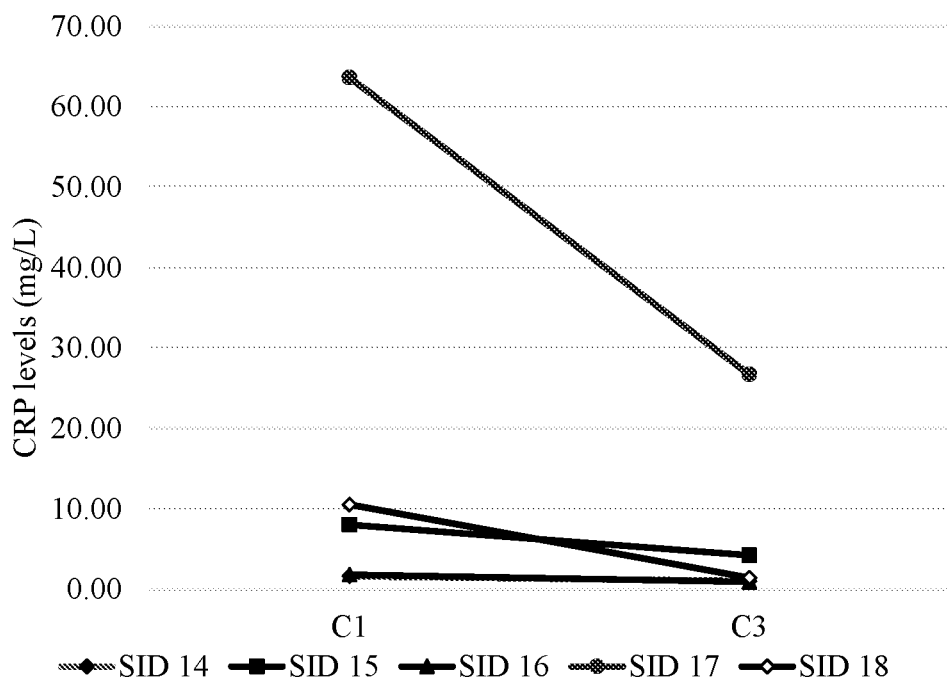

FIGS. 4A-4C depict the levels of C-reactive protein (CRP), an inflammatory marker, of each evaluable patient at respective treatment cycles C1, C3, C5 and/or C7.

Figure 5A:
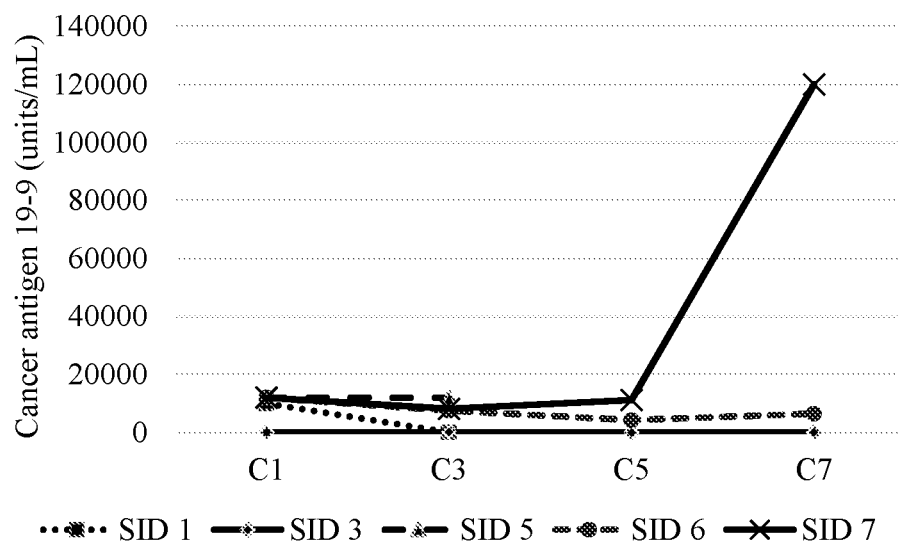
FIGS. 5A-5C depict the levels of cancer antigen 19-9 (CA 19-9) (units/mL) of each subject at the end of different treatment cycles (cycle 1, C1; cycle 3, C3; cycle 5, C5; and/or cycle 7, C7).
Figure 5B:
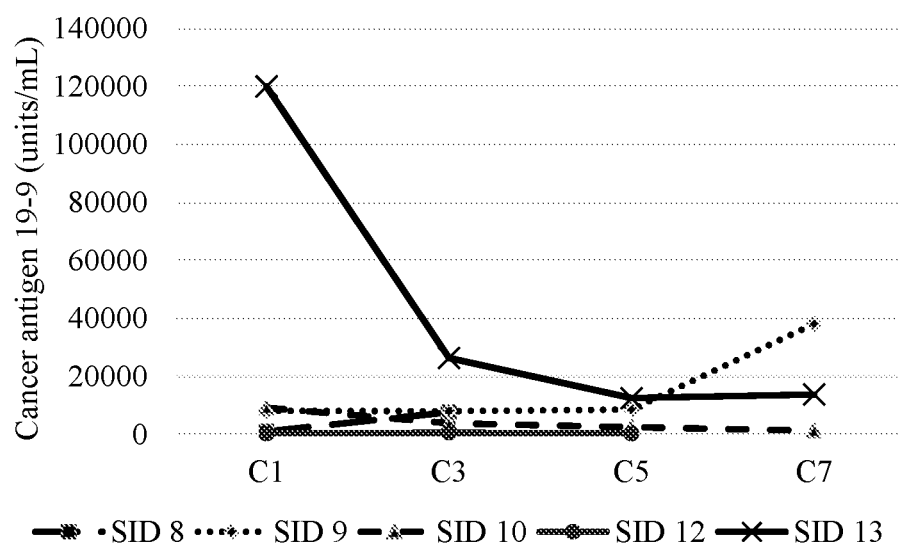
Figure 5C:
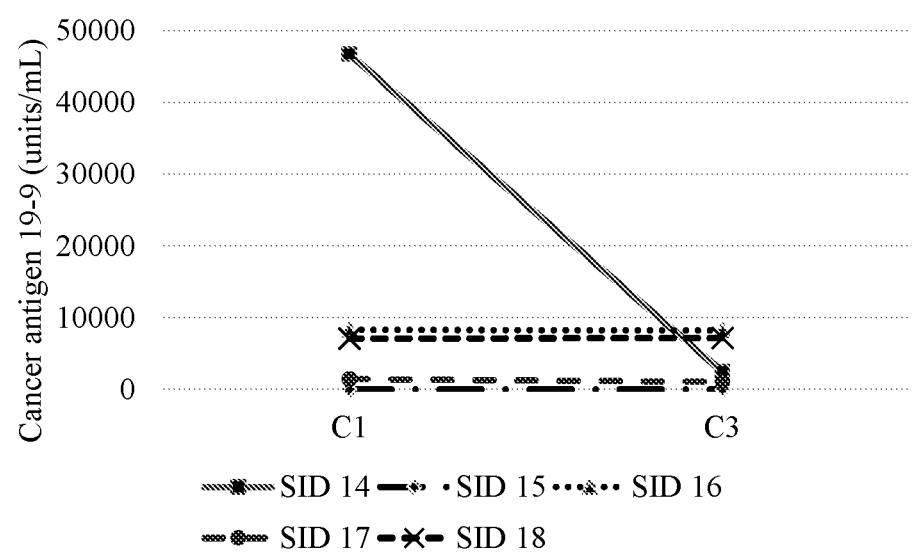

FIGS. 5A-5C depict the levels of cancer antigen 19-9 (CA 19-9) of each evaluable patient at respective treatment cycles C1, C3, C5 and/or C7.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

The invention claimed is:

1. A method for treating, inhibiting and/or reducing the severity of pancreatic cancer cachexia in a subject in need thereof comprising administering an effective amount of an inhibitor of IL-1 pathway to the subject, wherein the inhibitor comprises an anti-IL-1β antibody or an IL-1β-binding fragment thereof.

2. The method of claim 1 further comprising administering a chemotherapeutic agent, a chemotherapy protective drug, or both.

3. The method of claim 1, wherein the subject has been treated with a chemotherapeutic agent and/or a chemotherapy protective drug, prior to the administration of the inhibitor of the IL-1 pathway.

4. The method of claim 3, wherein the subject's response to the chemotherapeutic agent and/or the chemotherapy protective drug was ineffective prior to the administration of the inhibitor of the IL-1 pathway.

5. The method of claim 1, wherein the inhibitor of the IL-1 pathway further comprises an anti-IL-1α antibody, an IL-1 receptor antagonist, or a combination thereof.

6. The method of claim 1, wherein the anti-IL-1β antibody is selected from the group consisting of canakinumab, gevokizumab (VPM087) LY2189102, and a combination thereof.

7. The method of claim 2, wherein the chemotherapeutic agent comprises irinotecan and 5-fluoroucil, and the chemotherapy protective drug comprises folinic acid, and the cancer cachexia is pancreatic cancer cachexia.

8. The method of claim 1, further comprising selecting a subject having been diagnosed or shown symptoms of pancreatic cancer and exhibiting at least 5% weight loss within the six months prior, before the administration.

9. A method for treating, inhibiting and/or reducing the severity of pancreatic cancer in a subject in need thereof comprising administering an effective amount of an inhibitor of IL-1 pathway, wherein the inhibitor comprises an anti-IL-1β antibody or an IL-1β-binding fragment thereof.

10. The method of claim 9 further comprising administering a chemotherapeutic agent, a chemotherapy protective drug, or both.

11. The method of claim 9, wherein the subject has been treated with a chemotherapeutic agent and/or a chemotherapy protective drug, prior to the administration, and the subject's response to the chemotherapeutic agent and/or the chemotherapy protective drug was ineffective prior to the administration of the inhibitor of the IL-1 pathway.

12. The method of claim 9, wherein the anti-IL-1β antibody is selected from the group consisting of canakinumab, gevokizumab (VPM087), LY2189102, and a combination thereof, and the cancer is pancreatic cancer.

13. The method of claim 10, wherein the chemotherapeutic agent comprises irinotecan and 5-fluoroucil, and the chemotherapy protective drug comprises folinic acid.

14. The method of claim 1, further comprising selecting a subject having been diagnosed or shown symptoms of pancreatic cancer and exhibiting at least 5% weight loss within the six months prior, before the administration.

15. The method of claim 9, wherein the inhibitor of the IL-1 pathway is administered at a dose of about 0.1-1 mg/kg, 1-2 mg/kg, 2-3 mg/kg, 3-4 mg/kg, 4-5 mg/kg, 5-6 mg/kg, 6-7 mg/kg, 7-8 mg/kg, 8-9 mg/kg, 9-10 mg/kg, 10-11 mg/kg, 11-12 mg/kg, 12-13 mg/kg, 13-15 mg, 15-20 mg/kg or 20-25 mg/kg.

16. The method of claim 9, wherein the subject is a human.

17. The method of claim 9, wherein the inhibitor of the IL-1 pathway is administered for 1 month, 2 months, 3 months, 4 months, 5 months 6 months, 7 months, 8 months, 9 months, 10 months, 11 months, 12 months, 14 months, 16 months, 18 months, 20 months, 22 months, or 24 months.

* * * * *